(12) United States Patent
Nemoto et al.

(10) Patent No.: US 7,569,706 B2
(45) Date of Patent: Aug. 4, 2009

(54) GLYCEROL DERIVATIVE

(75) Inventors: Hisao Nemoto, Tokushima (JP); Motoo Yamasaki, Tokyo (JP); Toshiyuki Suzawa, Tokyo (JP); Hiroyuki Yamaguchi, Tokyo (JP)

(73) Assignees: Kyowa Hakko Kirin Co., Ltd., Tokyo (JP); Tecno Network Shikoku Co., Ltd., Kagawa (JP)

( * ) Notice: Subject to any disclaimer, the term of this patent is extended or adjusted under 35 U.S.C. 154(b) by 566 days.

(21) Appl. No.: 10/529,216

(22) PCT Filed: Sep. 2, 2003

(86) PCT No.: PCT/JP03/11214
§ 371 (c)(1),
(2), (4) Date: Mar. 25, 2005

(87) PCT Pub. No.: WO2004/029018
PCT Pub. Date: Apr. 8, 2004

(65) Prior Publication Data
US 2005/0208015 A1    Sep. 22, 2005

(30) Foreign Application Priority Data
Sep. 26, 2002    (JP)    ............ P.2002-281364

(51) Int. Cl.
C07D 207/08    (2006.01)
C07C 231/02    (2006.01)
C07C 29/03    (2006.01)

(52) U.S. Cl. .................. 548/530; 568/854; 564/152
(58) Field of Classification Search ............. 514/2; 548/473, 530; 564/152; 568/854
See application file for complete search history.

(56) References Cited

U.S. PATENT DOCUMENTS

2006/0280784 A1 * 12/2006 Nemoto et al. ............ 424/450

FOREIGN PATENT DOCUMENTS

| JP | 8-325271 | 12/1996 |
|----|----------|---------|
| WO | WO 98/28978 | 7/1998 |

OTHER PUBLICATIONS

Carnahan, et al., "Synthesis and Characterization of Polyether—Ester Dendrimers from Glycerol and Lactic Acid", *J. Am. Chem. Soc.*, vol. 123, No. 12 (2001), pp. 2905-2906.
Wang, et al., "Stabilization of Inorganic Nanocrystals by Organic Dendrons", *Journal of the American Chemical Society*, vol. 124, No. 10 (2002), pp. 2293-2298.
Yamasaki, et al., "Modification of Recombinant Human Granulocyte Colony-Stimulating . . . ", *J. Biochem.*, vol. 115 (1994), pp. 814-819.
Francis, et al., "PEG-Modified Proteins", *Pharmaceutical Biotechnology* (1992), pp. 235-263.

Inada, et al., "Ester Synthesis Catalyzed by Polyethylene . . . ", *Biochem. Biophys. Res. Commun.*, vol. 122, No. 2 (1984), pp. 845-850.
Knauf, et al., "Relationship of Effective Molecular Size to Systemic Clearance in Rats of . . . ", *J. Biol. Chem.*, vol. 263, No. 29 (1988), pp. 15064-15070.
Pettit, et al., "Structure-function studies of Interleukin 15 using Site-specific", *J. Biol. Chem.*, vol. 272, No. 4 (1997), pp. 2312-2318.
Yu, et al., "Polymeric micelles for drug delivery: solubilization and . . . " *J. Control. Release*, vol. 53 (1998), pp. 131-136.
Kajtár, et al., "Aggregation of Amphoetericin B in the Presence of γ-Cyclodextrin", *Biopolymers*, vol. 28 (1989), pp. 1585-1596.
Yokoyama, et al., "Characterization and Anticancer Activity of the . . . ", *Cancer Research*l, vol. 50 (1990), pp. 1693-1700.
Carnahan, et al., "Synthesis and Characterization of Poly(glycerol-succinic acid) Dendrimers", *Macromolecules*, vol. 34 (2001), pp. 7648-7655.
Morgan, et al., "Divergent Synthesis of Biodendrimers from Glycerol . . . ", *Polymer Preprints*, vol. 42, No. 2 (2001), pp. 155-156.
Carnahan, et al., "Biologically inspired Dendrimers Based on Glycerol . . . ", *Polymer Preprints*, vol. 42, No. 2 (2001), pp. 157-158.

(Continued)

*Primary Examiner*—James O Wilson
*Assistant Examiner*—Ebenezer Sackey
(74) *Attorney, Agent, or Firm*—Fitzpatrick, Cella, Harper & Scinto

(57) ABSTRACT

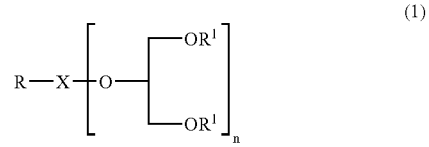

(wherein R represents a residue comprising a reactive group or a group capable of being transformed into the reactive group; n represents an integer of 3 or more; and X represents a residue capable of having the following structure by n in number:

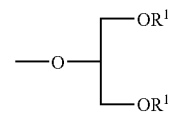

$R^1$s each represent a hydrogen atom or a group capable of being transformed into a hydrogen atom, and 6 or more of $R^1$s may be the same or different)

The compound represented by the above formula (1), which is capable of modifying a physiologically active polypeptide or a derivative thereof, or a low molecular compound while maintaining the physiological activity, or which is useful for improving the stability or water-solubility of the low molecular compound, are provided.

10 Claims, 1 Drawing Sheet

OTHER PUBLICATIONS

Grayson, et al., "Synthesis and Surface Functionalization of Aliphatic Polyether Dendrons", *J. Am. Chem. Soc.*, vol. 122 (2000), pp. 10335-10344.

Ling-Ling, et al., "A facile convergent route to dendritic polyols", *Chinese Journal of Chemistry*, vol. 16, No. 1 (1998), pp. 28-33.

Nemoto, et al., "Design and Synthesis of Cholestane Derivatives Bearing a . . .", *Bioorg. Med. Chem. Lett.*, vol. 9 (1999), pp. 205-208.

Das, et al., "Synthesis of a soluble boron neutron capture therapy . . .", *Journal of Organometallic Chemistry*, vol. 614-615 (2000), pp. 255-261.

Malenfant, et al., "Dendrimers as Solubilizing Groups for Conducting Polymers: Preparation and Characterization . . ." *Macromolecules*, vol. 33, No. 10 (2000), pp. 3634-3640.

Malenfant, et al., "Dendrimer-Supported Oligothiophene Synthesis: Aliphatic Ether Dendrimers in the . . .", *Chem. Mater.*, vol. 11, No. 12 (1999), pp. 3420-3422.

Malenfant, et al., "Dendrimer-Supported Solution Synthesis of Oligothiophenes without Beta Substituents", *Polymeric Materials Science and Engineering*, vol. 80 (1999), pp. 171-172.

* cited by examiner

```
SEQUENCE LISTING

<160> NUMBER OF SEQ ID NOS: 2

<210> SEQ ID NO 1
<211> LENGTH: 175
<212> TYPE: PRT
<213> ORGANISM: Artificial Sequence
<220> FEATURE:
<223> OTHER INFORMATION: Peptide substituted on 5 amino acids of hG-CSF

<400> SEQUENCE: 1

Met Ala Pro Thr Tyr Arg Ala Ser Ser Leu Pro Gln Ser Phe Leu Leu
 -1   1               5                  10                  15

Lys Ser Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu His
65                  70                  75

Ser Gly Leu Phe Leu Tyr Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Arg Arg Ala Gly Gly Val Leu Val Ala Ser His Leu Gln Ser
    145                 150                 155

Phe Leu Glu Val Ser Tyr Arg Val Leu Arg His Leu Ala Gln Pro
160                 165                 170

<210> SEQ ID NO 2
<211> LENGTH: 174
<212> TYPE: PRT
<213> ORGANISM: Artificial Sequence
<220> FEATURE:
<223> OTHER INFORMATION: Peptide substituted on 5 amino acids of hG-CSF

<400> SEQUENCE: 2

Ala Pro Thr Tyr Arg Ala Ser Ser Leu Pro Gln Ser Phe Leu Leu Lys
  1               5                  10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
                35                  40                  45

Leu Leu Gly His Ser Leu Gly Ile Pro Trp Ala Pro Leu Ser Ser Cys
            50                  55                  60

Pro Ser Gln Ala Leu Gln Leu Ala Gly Cys Leu Ser Gln Leu His Ser
```

| | | | | | | | | | | | | | | | |
|---|---|---|---|---|---|---|---|---|---|---|---|---|---|---|---|
| | | 65 | | | | 70 | | | | 75 | | | | 80 | |
| Gly | Leu | Phe | Leu | Tyr | Gln | Gly | Leu | Leu | Gln | Ala | Leu | Glu | Gly | Ile | Ser |
| | | | | 85 | | | | | 90 | | | | | 95 | |
| Pro | Glu | Leu | Gly | Pro | Thr | Leu | Asp | Thr | Leu | Gln | Leu | Asp | Val | Ala | Asp |
| | | | 100 | | | | | 105 | | | | | 110 | | |
| Phe | Ala | Thr | Thr | Ile | Trp | Gln | Gln | Met | Glu | Glu | Leu | Gly | Met | Ala | Pro |
| | | 115 | | | | | 120 | | | | | 125 | | | |
| Ala | Leu | Gln | Pro | Thr | Gln | Gly | Ala | Met | Pro | Ala | Phe | Ala | Ser | Ala | Phe |
| | 130 | | | | | 135 | | | | 140 | | | | | |
| Gln | Arg | Arg | Ala | Gly | Gly | Val | Leu | Val | Ala | Ser | His | Leu | Gln | Ser | Phe |
| 145 | | | | | 150 | | | | | 155 | | | | | 160 |
| Leu | Glu | Val | Ser | Tyr | Arg | Val | Leu | Arg | His | Leu | Ala | Gln | Pro | | |
| | | | | 165 | | | | | 170 | | | | 174 | | |

GLYCEROL DERIVATIVE

TECHNICAL FIELD

The present invention relates to a compound which is useful in chemically modifying a physiologically active polypeptide or a derivative thereof or a low molecular compound. Also, the present invention relates to a chemically modified polypeptide or a chemically modified low molecular compound in which a physiologically active polypeptide or a derivative thereof or a low molecular compound is modified with at least one of the compound, and a pharmaceutical composition which comprises the chemically modified polypeptide or the chemically modified low molecular compound. Furthermore, the present invention relates to a method for improving the stability or water-solubility of a physiologically active polypeptide or a derivative thereof or a low molecular compound, which comprises chemically modifying the physiologically active polypeptide or the derivative thereof or the low molecular compound with the compound.

BACKGROUND ART

Polypeptides having physiological activity are useful as therapeutic agents for specified diseases, but there are many cases in which sufficient pharmacological effects cannot be expected because of their poor stability when they are administered into blood. For example, there is a case in which the physiological activity is lost due to degradation by a hydrolase or the like existing in blood. Further, in the case of exogenous physiologically active polypeptides, their physiological activities are sometimes effective in treating diseases. However, since structures of such exogenous polypeptides, polypeptides produced by gene recombination, and the like are different from those of endogenous polypeptides, it is known that they induce an immune response when administered into blood and sometimes cause serious side effects such as anaphylactic shock or the like. In addition, among the physiologically active polypeptides, there are many polypeptides in which physical properties such as poor solubility or the like become problems when they are used as therapeutic agents.

As one of the methods for solving these problems in using a physiologically active polypeptide as a therapeutic agent, a method in which an inactive polymer chain such as polyethylene glycol is chemically bound to the polypeptide is firstly known.

For example, polyethylene glycol modification of a granulocyte colony-stimulating factor (G-CSF) is known [*Journal of Biochemistry*, 115, 814-819 (1994)]. Additionally, examples of the polyethylene glycol modification of asparaginase, glutaminase, adenosine deaminase, uricase or the like have been reported [*Pharmaceutical Biotechnology*, Volume 3, Stability of Protein Pharmaceuticals, Part B, In Vivo Pathways of Degradation and Strategies for Protein Stabilization, edited by Tim J. Ahern and Mark C. Manning, (USA), Plenum Publishing Co., November 1992, pp. 235-263]. As the effects obtained by modifying physiologically active polypeptides with a polyalkylene glycol, increase in heat stability [*Biophysics*, 38, 208 (1998)], solubilization in organic solvents [*Biochemical and Biophysical Research Communications*, 122, 845 (1984)] and the like are also known, in addition to the improvement of sustainability in blood, reduction of antigenicity and immunogenicity, improvement of stability in blood and the like.

However, when a physiologically active polypeptide is modified with a polyalkylene glycol, it is difficult in many cases to improve blood stability without decreasing physiological activity of the polypeptide. In general, it is known that blood sustainability of the polypeptide is improved as the molecular weight of a polyalkylene glycol becomes large or the degree of modification becomes large [*Journal of Biochemistry*, 263, 15064 (1988)], but the physiological activity of the polypeptide is decreased in some cases when the degree of modification is increased. It is considered that the modification of specific amino acid residues such as an amino group, a mercapto group, or the like which are necessary for the physiological activity, by a chemically modifying agent, the inhibition of the interaction at the physiologically active site by the polyalkylene glycol bound to the physiologically active polypeptide, or the like, are responsible therefor. Interleukin-15 is known as an example in which its physiological activity is reduced depending on the degree of modification [*Journal of Biochemistry*, 272, 2312 (1997)]. Thus, chemical modification has many advantages, but since the physiological activity of the polypeptide is generally decreased by the chemical modification, a chemically modifying agent which does not decrease the physiological activity of the polypeptide when its modification is carried out is desired.

On the other hand, it is sometimes difficult to prepare an aqueous solution of a low molecular compound having a concentration thereof capable of showing the physiological activity because many low molecular compounds have low water-solubility. In addition, even when an aqueous solution may once be prepared, there is a case in which the precipitate is formed during its preservation, thus causing substantial reduction of the concentration in a solution. For example, compound such as many anticancer agents, antibiotics, antiviral agents and the like are exemplified as such compounds. Accordingly, when a physiochemical test is carried out or a therapeutic agent is administered to the living body, it is probable that not only the intended effective concentration cannot be obtained, but also there is a case in which the pharmacological effect of interest cannot be achieved. Thus, attempts have been made to use low molecular compounds which hardly dissolve in water by solubilizing them through mixing with or chemically binding to a polymer or a surfactant. For example, a case is known in which a copolymer of polyethylene oxide and aspartic acid was used for the solubilization of amphotericin B [*Journal of Controlled Release*, 53, 131-136 (1998)]. Also, a case is known in which cyclodextrin was used for the solubilization of amphotericin B [*Biopolymers*, 28, 1585-1596 (1989)]. In addition, bile acid micelle and the like are also used for the solubilization of low molecular compounds such as cholesterol or the like. Polyethylene glycol and the like are also used for improving solubility of an anticancer agent [*Cancer Research*, 50, 1693-1700 (1900)]. As described above, methods and reagents for the solubilization of low molecular compounds without decreasing their physiological activities are desired. Also, a method in which a solubilizing agent is added as described above requires a necessity to take into consideration a problem of reproducibility and an influence of the solubilizing agent itself. Accordingly, reagents and methods capable of improving solubility or stability by chemically modifying low molecular compounds themselves are desired.

On the other hand, dendrimers having glycerol in their structures are known [*Macromolecules*, 34, 7648-7655 (2001); *Polymer Preprints*, 42, 155-156 (2001); *Polymer Preprints*, 42, 157-158 (2001); *Journal of American Chemical*

*Society*, 123, 2905-2906 (2001); *Journal of American Chemical Society*, 122, 10335-10344 (2000); *Chinese Journal of Chemistry*, 16, 28-33 (1998)].

DISCLOSURE OF THE INVENTION

Since considerable reduction of physiological activities is sometimes found in the chemically modified physiologically active polypeptides prepared by using conventional chemically modifying agents, a chemical modification method which does not decrease the physiological activity is desired. Also, a method which can improve water-solubility of a large number of low molecular compounds which hardly dissolve in water is desired.

The present invention relates to the following (1) to (30).
(1) A compound represented by formula (1):

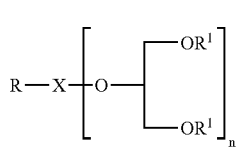

wherein R represents a residue comprising a reactive group or a group capable of being transformed into the reactive group; n represents an integer of 3 or more; and X represents a residue capable of having the following structure by n in number:

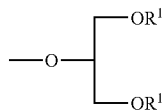

$R^1$s each represent a hydrogen atom or a group capable of being transformed into a hydrogen atom, and 6 or more of $R^1$s may be the same or different.

(2) The compound according to the above-described (1), wherein each $R^1$ represents a hydrogen atom.
(3) The compound according to the above-described (1), wherein each $R^1$ represent benzyl.
(4) The compound according to any one of the above-described (1) to (3), wherein n is $2^m$, in which m is an integer of 2 or more.
(5) The compound according to any one of the above-described (1) to (4), wherein X comprises one or more series branched structure.
(6) The compound according to any one of the above-described (1) to (5), wherein X comprises one to (n−1) structure(s) represented by

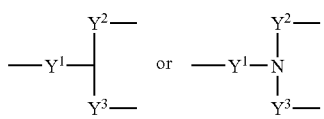

wherein $Y^1$, $Y^2$ and $Y^3$ each independently represent a single bond, or one, or two or more in any combination, which may be the same or different, selected from the group consisting of substituted or unsubstituted alkylene, carbonyl, substituted or unsubstituted imino, O, S, sulfonyl and sulfinyl, and when $Y^1$, $Y^2$ and $Y^3$ exist two or more in number, they may be the same or different.

(7) The compound according to any one of the above-described (1) to (6), wherein X comprises one to (n−1) structure(s) represented by

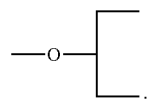

(8) The compound according to any one of the above-described (1) to (7), wherein X comprises one to (n−1) structure(s) represented by

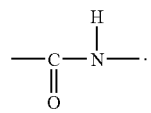

(9) The compound according to any one of the above-described (1) to (8), wherein X comprises one to (n−1) structure(s) represented by

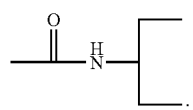

(10) The compound according to any one of the above-described (1) to (9), wherein X comprises one to (n−1) structure(s) represented by

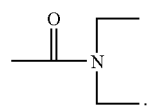

(11) The compound according to any one of the above-described (1) to (10), wherein the residue comprising a reactive group or a group capable of being transformed into the reactive group is a residue comprising a group having reactivity to or a group capable of being transformed into the group having reactivity to an amino acid side chain, an N-terminal amino group or a C-terminal carboxyl group in a physiologically active polypeptide or a derivative thereof, or a sugar chain bound to the polypeptide.

(12) The compound according to any one of the above-described (1) to (11), wherein the residue comprising a reactive group or a group capable of being transformed into the reactive group is selected from the group consisting of a carboxylic acid active ester residue, carbonate, maleimido, mercapto, formyl, tresyl, isocyanato, an acid anhydride residue, an acid halide residue, vinylsulfonyl, hydrazido, amino, a hydroxyl group, halogen, carboxy, vinyl and phosphono.

(13) A mixture comprising at least two compounds according to any one of the above-described (1) to (12).

(14) A compound represented by formula (2):

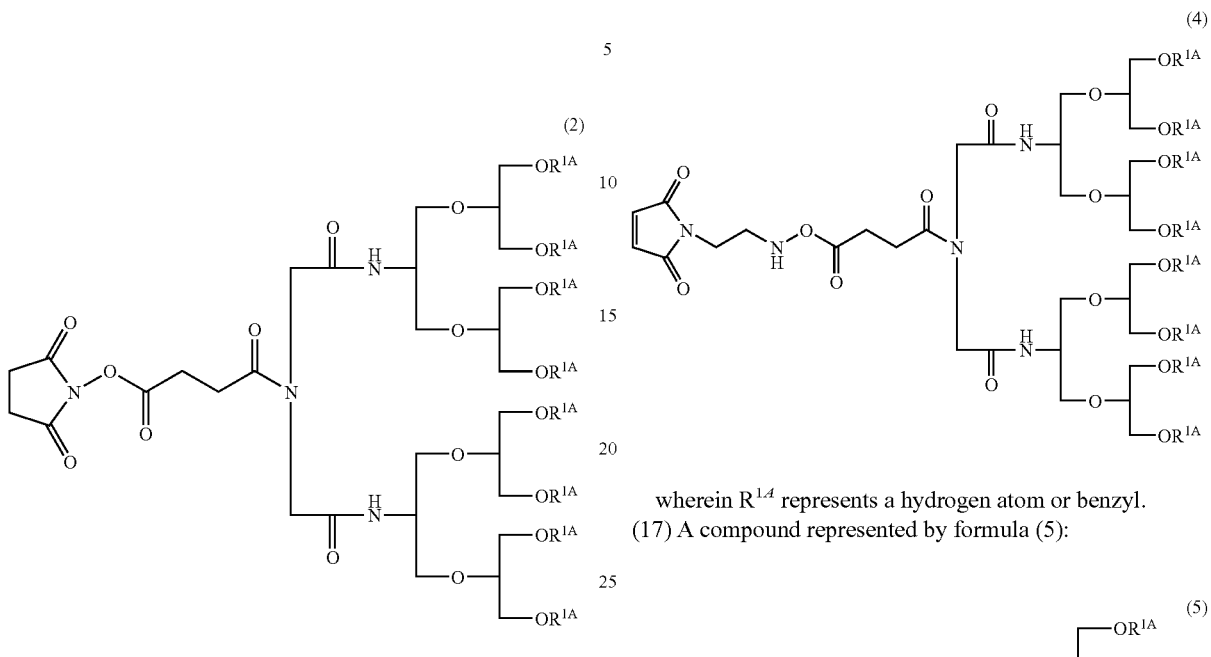

wherein $R^{1A}$ represents a hydrogen atom or benzyl.

(15) A compound represented by formula (3):

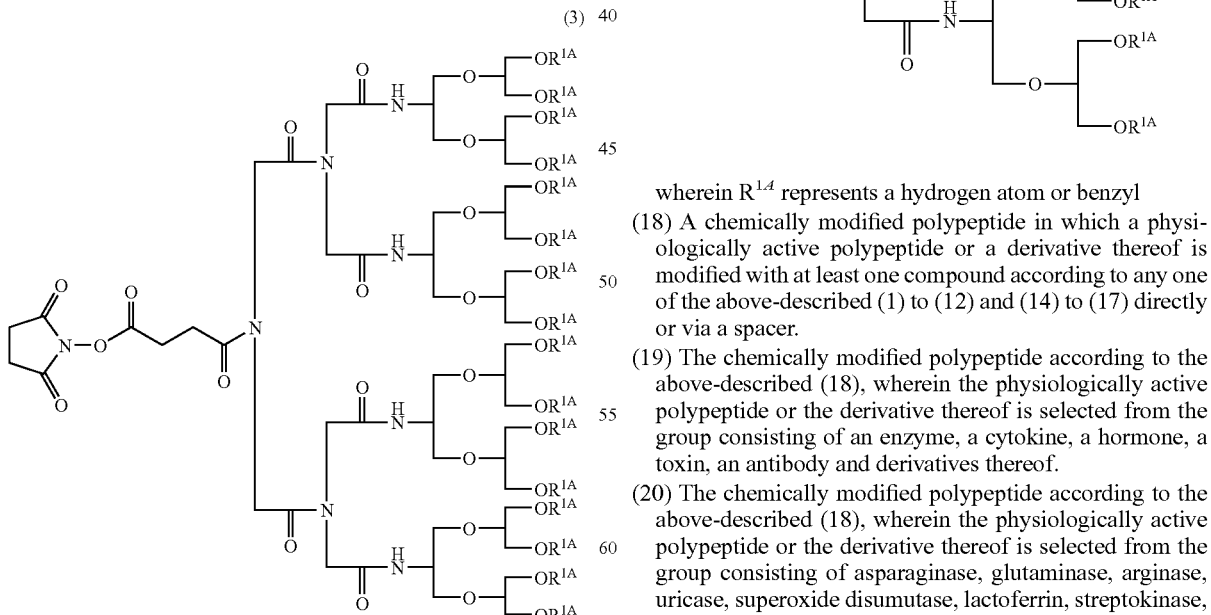

wherein $R^{1A}$ represents a hydrogen atom or benzyl.

(16) A compound represented by formula (4):

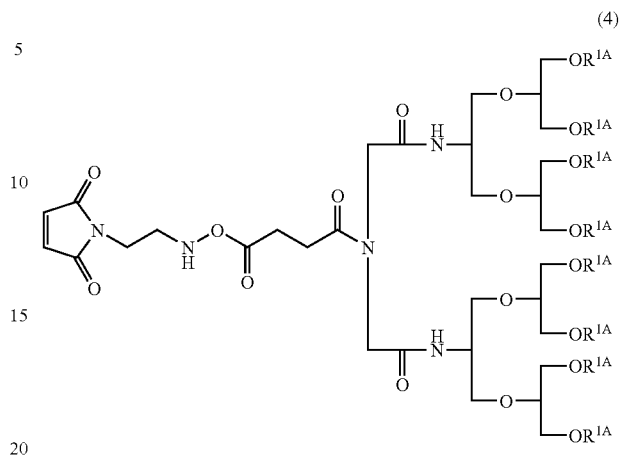

wherein $R^{1A}$ represents a hydrogen atom or benzyl.

(17) A compound represented by formula (5):

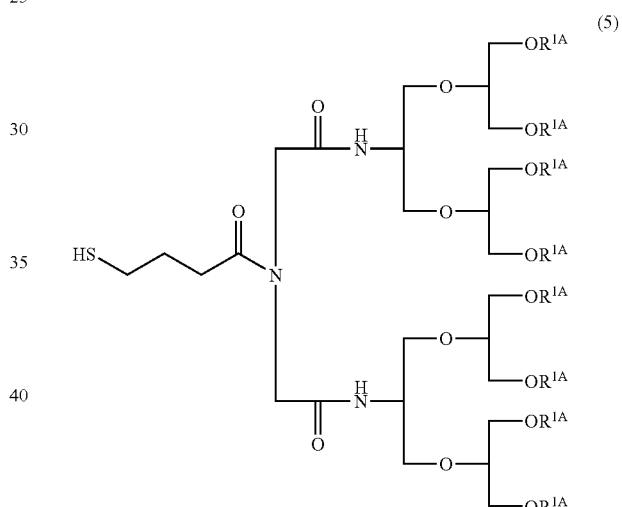

wherein $R^{1A}$ represents a hydrogen atom or benzyl

(18) A chemically modified polypeptide in which a physiologically active polypeptide or a derivative thereof is modified with at least one compound according to any one of the above-described (1) to (12) and (14) to (17) directly or via a spacer.

(19) The chemically modified polypeptide according to the above-described (18), wherein the physiologically active polypeptide or the derivative thereof is selected from the group consisting of an enzyme, a cytokine, a hormone, a toxin, an antibody and derivatives thereof.

(20) The chemically modified polypeptide according to the above-described (18), wherein the physiologically active polypeptide or the derivative thereof is selected from the group consisting of asparaginase, glutaminase, arginase, uricase, superoxide disumutase, lactoferrin, streptokinase, plasminin adenosine deaminase, interleukin-1 to 24, interferon-α, interferon-β, interferon-γ, interferon-ω, interferon-τ, granulocyte-colony stimulating factor, erythropoietin, tumor necrosis factor, thrombopoietin, klotho protein, leptin, fibroblast growth factor-1 to 19, midkine, calcitonin, epidermal growth factor, glucagons, insulin, insulin-like growth factor-1, osteogenic protein-1, stem cell growth factor, amylin, parathyroid hormone, plasminogen activators, vascular endothelial cell growth factor, transforming growth factors, glucagons-like peptides, growth hormone, natriuretic peptides, plasminogen, angiopoietin, angiostatin, endostatin, neocarzinostatin, hepatocyte growth factor, ricin, *Pseudomonas* exotoxin, diphtheria toxin, soluble receptors thereof and derivatives thereof.

(21) The chemically modified polypeptide according to any one of the above-described (18) to (20), wherein the derivative of a physiologically active polypeptide is selected from the group consisting of the polypeptide in which an amino acid is deleted, the polypeptide in which an amino acid is substituted, the polypeptide in which an amino acid is inserted, the polypeptide in which an amino acid is added, the polypeptide in which a sugar chain is deleted, and the polypeptide in which a sugar chain is bound.

(22) A pharmaceutical composition which comprises the chemically modified polypeptide according to any one of the above-described (18) to (21).

(23) A method for improving the stability or water-solubility of a physiologically active polypeptide or a derivative thereof which comprises chemically modifying the physiologically active polypeptide or the derivative thereof with the compound according to any one of the above-described (1) to (12) and (14) to (17).

(24) The method according to the above-described (23), wherein the physiologically active polypeptide or the derivative thereof is selected from the group consisting of an enzyme, a cytokine, a hormone, a toxin, an antibody and derivatives thereof.

(25) The method according to the above-described (23), wherein the physiologically active polypeptide or the derivative thereof is selected from the group consisting of asparaginase, glutaminase, arginase, uricase, superoxide disumutase, lactoferrin, streptokinase, plasmin, adenosine deaminase, interleukin-1 to 24, interferon-α, interferon-β, interferon-γ, interferon-ω, interferon-τ, granulocyte-colony stimulating factor, erythropoietin, tumor necrosis factor, thrombopoietin, klotho protein, leptin, fibroblast growth factor-1 to 19, midkine, calcitonin, epidermal growth factor, glucagons, insulin, insulin-like growth factor-1, osteogenic protein-1, stem cell growth factor, amylin, parathyroid hormone, plasminogen activators, vascular endothelial cell growth factor, transforming growth factors, glucagons-like peptides, growth hormone, natriuretic peptides, plasminogen, angiopoietin, angiostatin, endostatin, neocarzinostatin, hepatocyte growth factor, ricin, *Pseudomonas* exotoxin, diphtheria toxin, soluble receptors thereof, and derivatives thereof

(26) The method according to any one of the above-described (23) to (25), wherein the derivative of the physiologically active polypeptide is selected from the group consisting of the polypeptide in which an amino acid is deleted, the polypeptide in which an amino acid is substituted, the polypeptide in which an amino acid is inserted, the polypeptide in which an amino acid is added, the polypeptide in which a sugar chain is deleted, and the polypeptide in which a sugar chain is bound.

(27) A chemically modified low molecular compound in which a low molecular compound is modified with at least one compound according to any one of the above-described (1) to (12) and (14) to (17), directly or a via a spacer.

(28) A pharmaceutical composition which comprises the chemically modified low molecular compound according to the above-described (27).

(29) A method for improving the stability or water-solubility of a low molecular compound, which comprises chemically modifying the low molecular compound with the compound according to any one of the above-described (1) to (12) and (14) to (17).

(30) A chemically modifying agent for a physiologically active polypeptide or a derivative thereof or a low molecular compound which comprises the compound according to any one of the above-described (1) to (12) and (14) to (17).

In formula (1), $R^1$ represents a hydrogen atom or a group capable of being transformed into a hydrogen atom. The group capable of being transformed into a hydrogen atom includes, for example, substituted or unsubstituted lower alkyl, a substituted or unsubstituted alicyclic heterocyclic group, substituted or unsubstituted aralkyl, substituted or unsubstituted silyl, substituted or unsubstituted acyl, and the like. Among these, a hydrogen atom or benzyl is preferred as $R^1$.

The lower alkyl includes, for example, straight chain or branched chain alkyl having 1 to 8 carbon atom(s), such as methyl, ethyl, n-propyl, isopropyl, n-butyl, isobutyl, sec-butyl, tert-butyl, pentyl, neopentyl, hexyl, heptyl, octyl and the like.

The alicyclic heterocyclic group includes, for example, 3- to 8-membered monocyclic alicyclic heterocyclic groups containing at least one atom selected from a nitrogen atom, a oxygen atom and a sulfur atom, a bicyclic or tricyclic condensed-ring alicyclic heterocyclic group containing at least one atom selected from a nitrogen atom, a oxygen atom and a sulfur atom in which 3- to 8-membered rings are condensed, and the like, such as tetrahydropyridinyl, tetrahydroquinolinyl, tetrahydroisoquinolinyl, tetrahydropyranyl, tetrahydrofuranyl, dihydrobenzofuranyl, pyrrolidinyl, piperidino, piperidinyl, perhydroazepinyl, perhydroazosinyl, morpholino, morpholinyl, thiomorpholino, thiomorpholinyl, piperazinyl, homopiperidino, homopiperazinyl, dioxolanyl, imidazolidinyl, imidazolinyl, pyrazolidinyl, indolinyl, isoindolinyl, 2-pyrrolinyl, 2-pyrrolidonyl, 3-pyrrolidonyl, 2-piperidonyl, 3-piperidonyl, 4-piperidonyl, perhydro-2-azepinonyl, perhydro-3-azepinonyl, perhydroazepinonyl, 2-thiazolidonyl, 4thiazolidonyl, 2-oxazolidonyl, 4-oxazolidonyl, phthalimido, glutarimido, hydantoinyl, thiazolidinedionyl, oxazolidinedionyl and the like.

The aralkyl includes, for example, aralkyl having from 7 to 13 carbon atoms, such as benzyl, phenetyl, benzhydryl, naphthylmethyl and the like.

The acyl includes, for example, straight-chain, branched or cyclic acyl having 1 to 8 carbon atom(s), such as acetyl, propionyl, benzoyl and the like.

The substituents of the substituted lower alkyl, the substituted alicyclic heterocyclic group, the substituted aralkyl, the substituted silyl and the substituted acyl include, for example, 1 to 3 substituent(s) which may be the same or different, such as lower alkyl, lower alkoxy, lower alkoxy-lower alkoxy, aralkyloxy and the like. In this case, the lower alkyl moiety of the lower alkyl, the lower alkoxy and the lower alkoxy-lower alkoxy has the same meaning as the above-described lower alkyl, and the aralkyl moiety of the aralkyloxy has the same meaning as the above-described aralkyl.

In formula (1), X is not particularly limited, so long as it is a group capable of binding to R and the following structure by n in number:

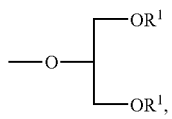

and it is preferred that it comprises at least one or more serially branched structure.

Also, the serially branched structure means a structure in which at least one branched chain of branched chains which are branched into two or more, is further branched into two or more, and this branching is repeated. Particularly, the preferred structure is a structure in which each of the branched chains which are branched into two or more is further branched into two or more, and this branching is repeated. In addition, it is preferred that the number of respective branches is 2.

As the branched structure,

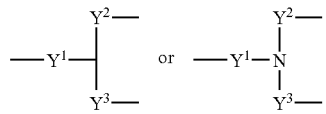

(wherein $Y^1$, $Y^2$ and $Y^3$ have the same meaning as described above, respectively) is preferred, and particularly

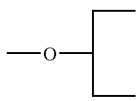

(hereinafter referred to as "glycerol unit")

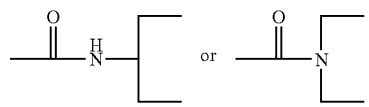

is more preferred. The number of these branched structures to be contained in formula (1) is not particularly limited, and is preferably one to (n−1), and when n is $2^m$, it is more preferably one to $(2^m-2)$.

In addition, a compound in which X in formula (1) comprises one to (n−1), or when n is $2^m$, one to $(2^m-2)$, of a structure represented by

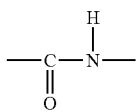

is also preferred.

Among the definitions of $Y^1$, $Y^2$ and $Y^3$, the alkylene includes, for example, straight-chain, branched or cyclic alkylene having 1 to 8 carbon atom(s), such as methylene, ethylene, n-propylene, isopropylene, n-butylene, isobutylene, sec-butylene, tert-butylene, pentylene, neopentylene, hexylene, heptylene, octylene, cyclopropylene, cyclobutylene, cyclopentylene, cyclohexylene, cyclopentylene, cyclooctylene and the like.

The substituents of the substituted alkylene includes, for example, 1 to 3 substituent(s) which may be the same or different, such as a halogen atom, lower alkyl, an unsaturated hydrocarbon group, aryl lower alkoxy, a hydroxyl group, oxo, carboxy, acyl, amino, nitro, cyano, and a heterocyclic group. In this case, the halogen atom includes atoms of fluorine, chlorine, bromine and iodine. The unsaturated hydrocarbon group includes, for example, a straight-chain, branched or cyclic unsaturated hydrocarbon group having 1 to 8 carbon atom(s), for example, alkenyl and alkynyl such as vinyl, allyl, 1-propenyl, methacryl 2-butenyl, 1-pentenyl, 2-hexenyl, 1,3-pentadienyl, 1,3-hexadienyl, cyclopentenyl, cyclopentadienyl, propargyl, pentynyl and the like. The aryl includes, for example, aryl having 6 to 14 carbon atoms, such as phenyl, naphthyl, antbranyl and the like. The heterocyclic group includes, for example, a 3- to 8-membered heterocyclic group and the like containing at least one hetero atom of a nitrogen atom, a oxygen atom, a sulfur atom and the like, such as furyl, thienyl, pyrrolyl, pyridyl, oxazolyl, thiazolyl imidazolyl, pyrimidinyl, triazinyl, indolyl, quinolyl, purinyl, benzoxazolyl, benzothiazolyl, benzoimidazolyl and the like. The lower alkyl and lower alkoxy have the same meaning as described above, respectively.

The substituents in the substituted imino include, for example, lower alkyl, aryl, aralkyl and the like. The lower alkyl, the aryl and the aralkyl have the same meaning as described above, respectively.

In formula (1), R is a residue comprising a reactive group capable of being transformed into the reactive group. The reactive group as a partial structure of R may be any group, so long as it can react with carboxy, amino, a hydroxyl or a derivative thereof or a low molecular compound. Examples include groups which are reactive to the side chain, the N-terminal amino group or the C-terminal carboxyl group of each amino acid, such as lysine, cysteine, arginine, histidine, serine, threonine, tryptophan, aspartic acid, glutamic acid, glutamine and the like in the polypeptide, and groups which are reactive to a sugar chain or the like bound to the polypeptide.

Preferred examples of the reactive group include a carboxylic acid active ester residue, carbonate, maleimido, mercapto, formyl, tresyl, isocyanato, an acid anhydride residue, an acid halide residue, vinylsulfonyl, hydrazido, amino, halogen and the like.

Preferred examples of the group capable of being transformed into a reactive group include a hydroxyl group, carboxy, amino, mercapto, formyl, vinyl phosphono, halogen and the like.

The carboxylic acid active ester of carboxylic acid active ester residue is ester having substituted or unsubstituted aryl, a substituted or unsubstituted heterocyclic group or the like. Examples include N-hydroxysuccinimide ester, p-nitrophenyl ester, thiophenyl ester, 2,3,5-trichlorophenyl ester, 2,4,6-trichlorophenyl ester, 2,4,5-trichlorophenyl ester, pentachlorophenyl ester, 2,4-dinitrophenyl ester, N-hydroxyphthalimido ester and the like.

The acid anhydride of the acid anhydride residue includes carboxylic anhydride and the like.

The acid halide residue includes carbonyl chloride, carbonyl bromide, carbonyl iodide, carbonyl fluoride and the like.

The R moiety other than the reactive group or the group capable of being transformed into the reactive group is not particularly limited, so long as it is a group which does not inhibit the reactivity, and it may be an optional group.

Examples include groups comprising one or two or more in optional combination, which may be the same or different, selected from the group consisting of a halogen atom, substituted or unsubstituted alkyl, a substituted or unsubstituted unsaturated hydrocarbon group, substituted or unsubstituted alkylene, substituted or unsubstituted aryl, substituted or unsubstituted alkoxy, a hydroxyl group, carbonyl, carboxy, substituted or unsubstituted acyl, substituted or unsubstituted amino, substituted or unsubstituted imino, nitro, cyano, O, S, sulfinyl, sulfonyl, a substituted or unsubstituted heterocyclic group and the like. Among these, groups comprising one or two or more in optional combination, which may be the same or different, selected from the group consisting of substituted or unsubstituted alkylene, carbonyl, substituted or unsubstituted imino, O and S are preferred.

The alkyl moiety of the alkyl and the alkoxy of B includes, for example, straight-chain, branched or cyclic alkyl having 1 to 8 carbon atom(s), such as methyl, ethyl, n-propyl, isopropyl, n-butyl, isobutyl, sec-butyl, tert-butyl, pentyl, neopentyl, hexyl, heptyl, octyl, cyclopropyl, cyclobutyl, cyclopentyl, cyclohexyl, cycloheptyl, cyclooctyl and the like.

The unsaturated hydrocarbon group, the alkylene, the halogen atom and the heterocyclic group have the same meanings as the unsaturated hydrocarbon group, the alkylene, the halogen atom and the heterocyclic group, respectively, described above in the definitions of $Y^1$, $Y^2$ and $Y^3$.

The aryl includes, for example, aryl having 6 to 14 carbon atoms, such as phenyl, naphthyl, biphenyl, anthranyl and the like.

The acyl has the same meaning as the acyl described above in the definition of $R^1$.

The substituent(s) of the substituted alkyl, the substituted unsaturated hydrocarbon group, the substituted alkylene, the substituted aryl, the substituted alkoxy, substituted acyl and the substituted heterocyclic group include, for example, 1 to 3 substituent(s) which may be the same or different, such as a halogen atom, alkyl, an unsaturated hydrocarbon group, aryl, alkoxy, a hydroxyl group, oxo, carboxy, acyl, amino, nitro, cyano, a heterocyclic group and the like, and the halogen atom, the alkyl, the unsaturated hydrocarbon group, the aryl, the alkoxy, the acyl and the heterocyclic group have the same meaning as described above, respectively.

The substituent of the substituted imino includes, for example, alkyl, an unsaturated hydrocarbon group, aryl, alkoxy, acyl, amino, a heterocyclic group and the like, the substituent of the substituted amino includes, for example, 1 or 2 substituent(s) which nay be the same or different, such as alkyl, an unsaturated hydrocarbon group, aryl, alkoxy, acyl, amino, a heterocyclic group and the like, and the alkyl, the unsaturated hydrocarbon group, the aryl, the alkoxy, the acyl and the heterocyclic group have the same meaning as described above, respectively.

In formula (1), n is not particularly limited, so long as it is an integer of 3 or more, and is preferably $2^m$, wherein m has the same meaning as described above, and is more preferably from 4 to 1,024 ($2^2$ to $2^{16}$).

The compound of the present invention may be a single compound or a mixture of compounds having different structures, and a single compound is preferred.

The molecular weight of the compound represented by formula (1) is not particularly limited, and the compound has preferably a molecular weight of 100 to 1,000,000, and more preferably 1,000 to 100,000.

Representative examples of the compound represented by formula (1) include compounds represented by the above-described formulae (2), (3), (4), (5) and the like.

The compound represented by formula (1) can be produced by a combination of reactions known in usual organic synthesis methods [*Organic Synthesis*, I to IV, edited by The Chemical Society of Japan, Mazen (1992)] and the like. As an example, the following general production method can be cited.

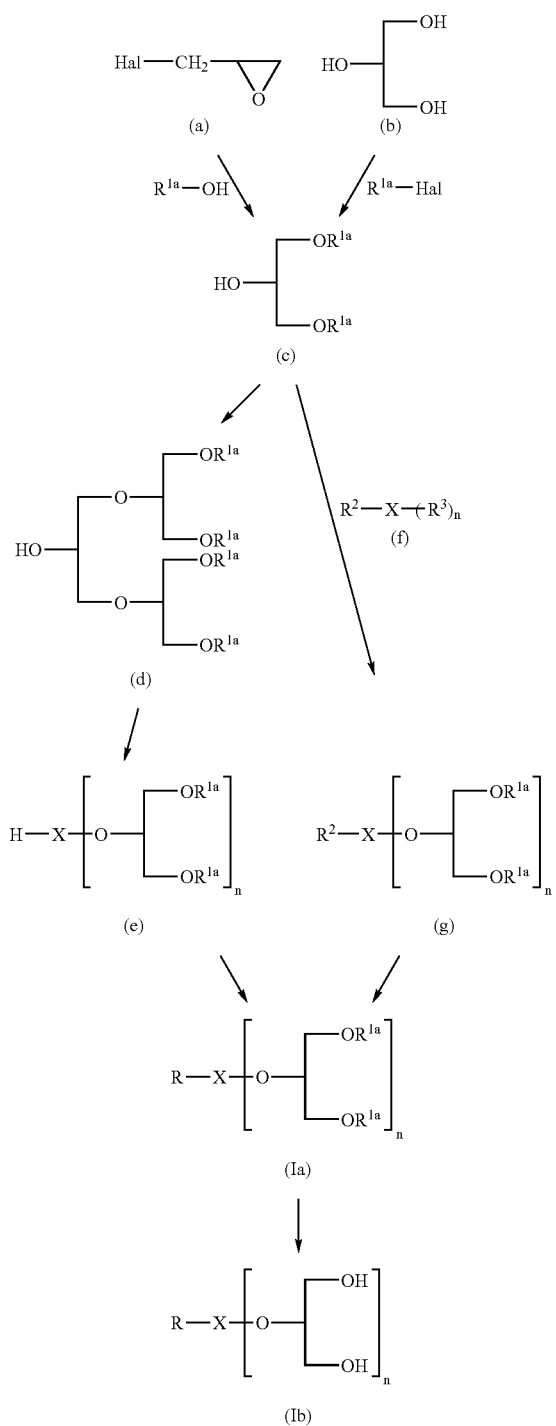

[wherein, R, X and n have the same meaning as described above, respectively; Hal represents a halogen atom; $R^{1a}$ represents a group capable of being transformed into a hydrogen atom; $R^2$ represents a group capable of being transformed into R; and $R^3$ represents a group which can be substituted with

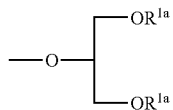

(wherein $R^{1a}$ has the same meaning as described above).]

The halogen atom and the group capable of being transformed into a hydrogen atom have the same meaning as described above, respectively. The group capable of being transformed into R is not particularly limited, so long as it is a group capable of being transformed into R, and examples include those described in the definition of the group capable of being transformed into a hydrogen atom, The group which can be substituted with

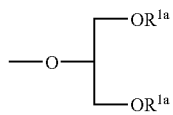

(wherein $R^{1a}$ has the same meaning as described above) is not particularly limited, so long as it is a group which can be substituted with

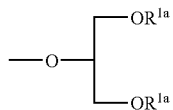

(wherein $R^{1a}$ has the same meaning as described above), and examples include a hydrogen atom, a halogen atom, a hydroxyl group, alkoxy, alkanoyloxy and the like, wherein the halogen atom has the same meaning as described above, and the alkyl moiety of the alkoxy and the alkanoyloxy has the same meaning as the above-described alkyl.

Compound (c) can be obtained in accordance with the methods described in *J. Org. Chem.*, 57, 435 (1992), *J. Med. Chem.*, 38 (10), 1673 (1995) and the like by using epihalohydrin (Compound (a)) such as epichlorohydrin, epibromohydrin, epifluorohydrin or the like and $R^{1a}$—OH (wherein $R^{1a}$ has the same meaning as described above). Also, Compound (c) can be obtained by allowing 1 mole of glycerol (compound (b)) to react with 1 to 10 mole(s) of $R^{1a}$—Hal (wherein $R^{1a}$ and Hal have the same meaning as described above, respectively) in the presence of an appropriate base and then purifying the product, or by allowing it to react with 2-methyl-1-butene in the presence of a catalytic amount of $BF_3$—$O(C_2H_5)_2$ [*Tetrahedron Lett.*, 29, 2951 (1988)], thereby selectively protecting a hydroxyl group of the primary alcohol, or in accordance with the methods described in *Tetrahedron Lett.*, 41, 6411 (2000), *J. Org. Chem.*, 54, 1346 (1989), *Can. J. Chem.*, 6, 241 (1984) and the like. In addition, Compound (c) can be obtained by protecting a hydroxyl group of the primary alcohol of compound (b) in accordance, for example, with the protective group introducing method described in *Protective Groups in Organic Synthesis*, third edition, edited by T. W. Greene, John Wiley & Sons, Inc. (1999) or the like.

As the $R^{1a}$—OH to be allowed to react with Compound (a), for example, various alcohols such as methanol, ethanol, propanol, tert-butyl alcohol, benzyl alcohol and the like can be used. Also, as the $R^{1a}$ of $R^{1a}$—Hal to be allowed to react with Compound (b), it is possible to use a residue which can be removed, such as benzyl, methyl, ethyl, propyl, tert-butyl, methoxymethyl, methoxyethoxymethyl, tetrahydropyranyl, tetrahydrofuranyl, triphenylmethyl, benzyloxymethyl, triethylsilyl or the like. Commercially available products can be used as Compounds (a) and (b), and Compound (c) can be synthesized in accordance with the above-described method or can be obtained as a commercially available product.

Next, Compound (d) is obtained by further reacting Compound (c) obtained by the above-described step with Compound (a), or by reacting Compound (b) with

(wherein Hal and $R^{1a}$ has the same meaning as described above, respectively).

By repeating this reaction step, Compound (e) wherein X comprises a serially branched structure, and n Compound (c) residues are bound to X can be obtained.

Compound (Ia) can be obtained by binding the residue R containing a reactive group or a group capable of being transformed into the reactive group to the X-terminal hydroxyl group existing in Compound (e), by using a general organic synthesis reaction, or by directly being transformed the hydroxyl group into a reactive residue.

On the other hand, Compound (g) can be obtained by reacting Compound (f) with Compound (c) synthesized in the similar manner as described above. The method for obtaining Compound (g) by reacting Compound (f) with Compound (c) includes a substitution reaction of the $R^3$ moiety of Compound (f) with Compound (c), a combination of reactions known in the general organic synthesis methods [*Organic Synthesis*, I to IV, edited by The Chemical Society of Japan, Maruzen (1992)] and the like. Compound (Ia) can be obtained by converting $R^2$ of Compound (g) into the residue R comprising a reactive group or a group capable of being transformed into the reactive group, by using a general organic synthesis reaction. A commercially available compound having a known structure can be used as Compound (f), or Compound (f) can be prepared by combining the reactions known in the general organic synthesis methods [Organic Synthesis, I to IV, edited by The Chemical Society of Japan, Maruzen (1992) and the like].

Compound (Ib) is obtained by subjecting Compound (Ia) to a protecting group removing reaction generally used in the organic synthesis reactions [e.g., *Protective Groups in Organic Synthesis*, third edition, edited by T. W. Greene, John Wiley & Sons, Inc. (1999) and the like] to thereby remove $R^1$ and replace it with a hydrogen atom.

On the contrary to this, in the formula(I), it is possible to produce the compound of the present invention by elongating the glycerol unit from the —$OR^1$ terminus, in the opposite direction of X.

Each reaction step is carried out in an appropriate solvent, preferably a solvent optionally selected from dichloromethane, chloroform, N,N-dimethylformamide, dimethyl sulfoxide, toluene, tetrahydrofuran, acetonitrile, methanol, ethanol, pyridine, water and mixed solvents thereof at a temperature of −20 to 150° C. for 1 hour to several days.

Each of the compounds obtained by respective steps can be used in the subsequent step with the purity as such, or after purifying it to an optional purity by general purification methods such as recrystallization, solvent extraction, silica gel chromatography, reverse phase chromatography, normal phase chromatography and the like.

The compound of the present invention can be used as a chemically modifying agent, for example, for the purpose of improving the stability or water-solubility of a physiologically active polypeptide, a low molecular compound or the like Specifically, the above-described object can be achieved by binding the compound of the present invention to carboxy, amino, a hydroxyl group, mercapto, formyl, phosphono or the like in a physiologically active polypeptide or a derivative thereof or a low molecular compound, directly or via a spacer.

An amino acid or a peptide is preferred as the spacer, but it may be other substance, so long as it can bind the compound of the present invention with carboxy, amino, a hydroxyl group, mercapto, formyl, phosphono or the like in a physiologically active polypeptide or a derivative thereof or a low molecular compound. As the amino acid, a natural amino acid such as lysine or cysteine or the like may be used, and ornithine, diaminopropionic acid, homocysteine or the like may also be used. More preferably, cysteine may be used. As the peptide, a peptide comprising 2 to 10 amino acid residues is preferred. The spacer other than the amino acid and peptide includes glycerol, ethylene glycol, saccharide and the like. The saccharide in this case includes a monosaccharide, a disaccharide and the like such as glucose, galactose, sorbose, galactosamine, lactose and the like.

These spacers are bound, for example, to the side chain of a residue such as lysine, cysteine, arginine, histidine, serine, threonine or the like in a physiologically active polypeptide or a derivative thereof via an amido bond, a thioether bond, an ester bond or the like, to the C-terminal carboxyl group of the polypeptide or the derivative thereof via an amido bond or an ester bond, or to the N-terminal amino group of the polypeptide or the derivative thereof via an amido bond. They can be bound by a usual peptide synthesis method [*The Basis and Experimentation of Peptide Synthesis*, edited by Izumiya et al., Maruzen (1985)] or a usual gene recombination method.

In this case, it is preferred to introduce, for example, an amino acid, a peptide or the like which becomes the spacer, into the C-terminal carboxyl group or the like of a physiologically active polypeptide or a derivative thereof, simultaneously with the synthesis of the physiologically active polypeptide or a derivative thereof, but the spacer can also be bound after synthesis of the physiologically active polypeptide or a derivative thereof. Alternatively, the C-terminal carboxyl group or the like of the polypeptide or a derivative thereof can be bound to a spacer after activating the former by means of a chemical synthesis. In addition, a spacer to which the compound of the present invention was bound in advance can be bound to a physiologically active polypeptide or a derivative thereof by the above-described method.

The physiologically active polypeptide or the derivative thereof used in the present invention includes an enzyme, a cytokine, a hormone, a toxin, an antibody, derivatives thereof and the like.

The physiologically active polypeptide includes, for example, asparaginase, glutaminase, arginase, uricase, superoxide disumutase, lactoferrin, streptokinase, plasmin, adenosine deaminase, interleukin-1 to 24, interferon-α, interferon-β, interferon-γ, interferon-ω, interferon-τ, granulocyte-colony stimulating factor, erythropoietin, tumor necrosis factor, thrombopoietin, klotho protein, leptin, fibroblast growth factor-1 to 19, midkine, calcitonin, epidermal growth factor, glucagons, insulin, insulin-like growth factor-1, osteogenic protein-1, stem cell growth factor, amylin, parathyroid hormone, plasminogen activators, vascular endothelial cell growth factor, transforming growth factors, glucagons-like peptides, growth hormone, natriuretic peptides, plasminogen, angiopoietin, angiostatin, endostatin, neocarzinostatin, hepatocyte growth factor, ricin, *Pseudomonas* exotoxin, diphtheria toxin, soluble receptors thereof, and the like.

The antibody used in the present invention can be prepared as a polyclonal antibody or a monoclonal antibody by using a known technique [*Antibodies-A Laboratory Manual*, Cold Spring Harbor Laboratory (1988)].

Any of a polyclonal antibody and a monoclonal antibody can be used as the antibody used in the present invention, and a monoclonal antibody is preferred.

The monoclonal antibody used in the present invention includes an antibody produced by a hybridoma, a humanized antibody, antibody fragments thereof and the like.

The humanized antibody includes a human chimeric antibody, a human complementarity determining region (hereinafter referred to as "CDR")-grafted antibody and the like.

A human chimeric antibody is an antibody which comprises a non-human antibody heavy chain variable region (hereinafter referred to as "VH", the heavy chain and the variable region being "H chain" and "V region", respectively) and a non-human antibody light chain variable region (hereinafter referred to as "VL", the light chain being "L chain"), a human antibody heavy chain constant region (hereinafter also referred to as "CH", the constant region being "C region") and a human antibody light chain constant region (hereinafter also referred to as "CL"). As the non-human animal, any animal such as mouse, rat, hamster or rabbit can be used, so long as a hybridoma can be prepared there from.

A human CDR-grafted antibody is an antibody in which amino acid sequences of CDRs of V regions of H chain and L chain of an antibody derived from a non-human animal are grafted into appropriate positions of V regions of H chain and L chain of a human antibody.

The antibody fragment includes Fab, Fab', F(ab')$_2$, a single chain antibody (hereinafter referred to as "scFv"), a disulfide-stabilized V region fragment (hereinafter referred to as "dsFv"), a peptide comprising CDR, and the like.

An Fab is a fragment having a molecular weight of about 50,000 and antigen binding activity, which is constituted by about a half of the N-terminal side of H chain and the entire L chain which are obtained by digesting with enzyme, papain upper peptide moieties of two disulfide bonds crosslinking two H chains in the hinge region of IgG.

An Fab' is a fragment having a molecular weight of about 50,000 and antigen binding activity, which is obtained by cutting a disulfide bond of the hinge region of the following F(ab')$_2$.

An F(ab')$_2$ is a fragment having a molecular weight of about 100,000 and antigen binding activity, which is constituted by two Fab regions bound at the hinge region which are obtained by digesting with enzyme, trypsin the lower moieties of two disulfide bonds in the hinge region of IgG.

An scFv is a VH-P-VL or VL-P-VH polypeptide in which one chain VH and one chain VL are bound by using an appropriate peptide linker (hereinafter referred to as "P"). As VH and VL comprised in the scFv used in the present invention, any of the monoclonal antibody or human CDR-grafted antibody of the present invention can be used.

A dsFV is a fragment in which polypeptides with one amino acid residue of each of VH and VL is substituted with a cysteine residue are bound via a disulfide bond. The amino acid residue which is substituted with a cysteine residue can be selected by estimating on a three-dimensional structure of the antibody in accordance with the method shown by Reiter el al. [*Protein Engineering*, 7, 697 (1994)]. As VH or VL contained in the disulfide-stabilized antibody used in the present invention, any of the monoclonal antibody and human CDR-grafted antibody can be used.

The antibody or antibody fragment thereof used in the present invention includes fusion antibodies in which a radioisotope, a protein, a drug or the like is chemically or genetically bound to the antibody or the antibody fragment, The derivative of the physiologically active polypeptide used in the present invention includes the physiologically active polypeptide in which an amino acid is deleted, the physiologically active polypeptide in which an amino acid is substituted, the physiologically active polypeptide in which an amino acid is inserted, the physiologically active polypeptide in which an amino acid is added, the physiologically active polypeptide in which a sugar chain is deleted, the polypeptide in which a sugar chain is bound, and the like. It is preferred that these derivatives have activity similar to that owned by the physiologically active polypeptide (hereinafter, both of the physiologically active polypeptide and the derivatives thereof being referred to as "physiologically active polypeptide").

The low molecular compound to be used in the present invention is not particularly limited, so long as it can be substituted with a part of R in the compound represented by formula (1) by reacting with the part of R. Examples include compounds having a functional group such as carboxy, primary or secondary amino, a hydroxyl group, mercapto, formyl, phosphono, a carboxylic acid active ester residue, an acid anhydride residue, halogen, an acid halide residue, isocyanato, maleimido, hydrazido or vinylsulfonyl.

As the low molecular compound, any compound can be used, so long as it is a low molecular compound. The molecular weight of the low molecular compound is not particularly limited, and it is preferably 50 to 10,000, and more preferably 100 to 2,000. Also, a preferred low molecular compound is one having insufficient water-solubility, which has such a solubility in water or an aqueous solution of 0 to 1 mol/l, preferably 0 to 0.1 mol/l and it is that at least 1.1 times or more, preferably from 10 to $10^3$ times, improvement of the value of solubility is expected. The low molecular compound includes sterols such as cholesterol, dihydrocholesterol, lanosterol, β-sitosterol, campesterol, stigmasterol, brassicasterol, ergocasterol, fucosterol and the like, antitumor agents such as cytosine arabinoside, doxorubicin, daunorubicin, aclarubicin, mitomycin, bleomycin, 5-fluorouracil, duocarmycin, methotrexate, camptotecin, taxan and the like; antibiotics such as ampicillin, cefalexin, cefaclor, gentamicin, streptomycin, kanamycin, amphotericin, penicillin, cefazolin and the like; antiviral agents such as ganciclovir, acyclovir and the like; derivatives thereof; and the like. The above-described derivatives include modified derivatives in which an optional functional group is deleted, substituted, inserted or added; modified derivatives modified with radioisotopes, drugs, saccharides and the like.; and the like, and it is preferred that they have the similar activity as the unmodified low molecular compounds.

These physiologically active polypeptides or low molecular compounds are produced in a buffer such as a phosphate buffer, a borate buffer, an acetate buffer, a citrate buffer or the like, or water, an appropriate organic solvent such as N,N-dimethylformamide, dimethyl sulfoxide, dioxane or tetrahydrofuran, or a mixed solvent of the organic solvent and an aqueous solution, and used in the chemical modification reaction [cf., *A Sequel to Protein Hybrid*, edited by Yuji Inada and Hiroshi Maeda, Kyoritsu Shuppan (1988)].

When the physiologically active polypeptides or low molecular compounds are chemically modified with the compounds of the present invention, chemically modified polypeptides, chemically modified low molecular compounds or the like to which one or more of the compounds were bound are obtained.

The physiologically active polypeptide or low molecular compound is chemically modified by reaction using from about 1 to 1,000 moles, preferably about 1 to 50 moles, of the compound of the present invention based on 1 mole of the physiologically active polypeptide or low molecular compound. Degree of the modification of a physiologically active polypeptide or low molecular compound by the compound can be optionally selected by adjusting the molar ratio of the compound to the physiologically active polypeptide or low molecular compound, reaction temperature, pH, reaction time and the like. Also, the solvent to be used in the reaction may be any solvent, so long as it does not inhibit the reaction, and is selected from, for example, a phosphate buffer, a borate buffer, a Tris-HCl buffer, an aqueous sodium hydrogencarbonate solution, a sodium acetate buffer, a citrate buffer, water, N,N-dimethylformamide, dimethyl sulfoxide, methanol, acetonitrile, dioxane, tetrahydrofuran and the like and mixed solvents thereof The temperature, pH and time of the reaction are not particularly limited, so long as they are such conditions that the activity of the physiologically active polypeptide or low molecular compound is not decreased, and it is preferred that the reaction is carried out, for example, at a temperature between 0 to 50° C. and at a pH value of 4 to 10 for 10 minutes to 100 hours.

The physiologically active polypeptide or low molecular compound modified with the compound of the present invention can be purified in accordance with the usual method such as gel filtration, ion exchange chromatography, reverse phase high performance liquid chromatography, affinity chromatography, ultrafiltration or the like. In addition, a chemically modified polypeptide, a chemically modified low molecular compound or the like having optional degree of chemical modification can also be purified by fractionating it according to these purification techniques.

The structure of the synthesized or purified physiologically active polypeptide or low molecular compound and the physiologically active polypeptide or the low molecular compound modified with the compound of the present invention can be confirmed by the amino acid composition analysis using mass spectrometry, nuclear magnetic resonance (NMR) and an amino acid analyzer, or by the amino acid sequence analysis or the like using reverse phase high performance liquid chromatography (HPLC) analysis of phenylthiohydantoin (PTH) amino acids obtained by carrying out Edman degradation using a gas phase protein sequencer.

The chemically modified polypeptides or chemically modified low molecular compounds prepared in the above can be used as pharmaceutical preparations such as diagnostic agents, therapeutic agents and the like. The therapeutic agents are expected to have certain effects such as reduction of antigenicity and immunogenicity, improvement of water-solubility, protease resistance, retaining of three-dimensional structure, stabilization in serum, inhibition of conjugate formation and the like, in addition to the maintenance and improvement of biological activity, reticuloendothelial system (RES) avoidance, improvement of blood persistence, smooth release of agents and reduction of toxicity.

The administration method of the chemically modified polypeptides or chemically modified low molecular compounds includes intravenous injection, oral administration and the like, although the administration method is not limited thereto.

Pharmaceutical compositions comprising the chemically modified polypeptides or chemically modified low molecular compounds include, for example, solutions, suspensions, emulsions, freeze-dried preparations and the like which are combined with a pharmaceutically acceptable substance for parenteral use. The substance includes water, a brine, a Ringer solution, a dextrose solution, 1 to 10% human serum albumin and the like. The substance may comprise an additive agent such as sodium chloride, mannitol, amino acid or the like for the purpose of keeping the isotonicity, or may contain a buffer, an antiseptic or the like for keeping the chemical stability. It is preferred to sterilize the pharmaceutical compositions in accordance with a usual method. The parenteral pharmaceutical composition suitable for injection administration is prepared by dissolving the above-described chemically modified polypeptide or chemically modified low molecular compound, an additive agent and the like, for example, in an aqueous solution containing 0.9% sodium chloride. The pharmaceutical composition is administered once or twice or more. The pharmaceutical composition is administered as a therapeutic agent or in combination with other therapeutic agents. Treatment by the pharmaceutical composition can be combined with a conventional treatment, and in this case, the treatment may be carried out by continuous or simultaneous administration.

The pharmaceutical compositions comprising the chemically modified polypeptide or chemically modified low molecular compound can also be prepared as tablets, pills or capsules prepared in combination with a pharmaceutically acceptable traditional diluent or base. The diluent or base may contain conventional excipients such as lactose, starch and magnesium stearate.

The dose or administration frequency varies depending on the chemically modified polypeptide or chemically modified low molecular compound to be used, intended therapeutic effect, administration method, treating period, age, body weight and the like, and the active ingredient is usually administered at a dose of 10 µg/kg to 8 mg/kg per day per adult.

The present invention is described based on Test Examples, Examples and Reference Examples, but the present invention is not limited thereto.

Figure 1:
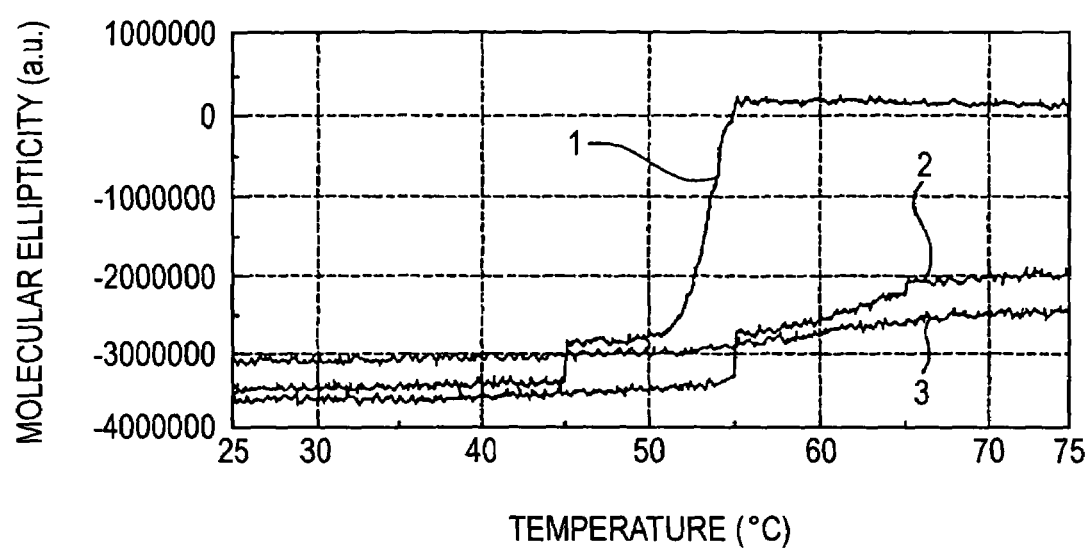
FIG. 1 is a graph showing changes in the circular dichroism polarization spectrum (ellipticity) of an inventive compound-modified G-CSF derivative, a polyethylene glycol-modified G-CSF derivative and unmodified G-CSF derivative, accompanied by the increase of temperature. The abscissa represents temperature (° C.), and the ordinate represents molecular ellipticity (a.u.), and meaning of each plot is as follows.

1: Unmodified G-CSF derivative
2: Polyethylene glycol-modified G-CSF derivative
3: Inventive compound-modified G-CSF derivative

BEST MODE FOR CARRYING OUT THE INVENTION

TEST EXAMPLE 1

Biological Activity Measurement of Chemically Modified G-CSF Derivatives:

Growth promoting activity of each G-CSF derivative prepared in Example 1, Reference Example 1 or Reference Example 2 upon a mouse leukemia cell NFS60 [*Proc. Natl. Acad. Sci. USA,* 82, 6687 (1985)] was measured in accordance with the method of Asano, et al. [*Pharmacology and Therapy,* 19, 2767 (1991)]. The activity of each compound when specific activity (U/mg) of the unmodified G-CSF derivative was defined as 100 is shown in Table 1. Specific activity of the conventional polyethylene glycol-modified sample was considerably reduced, but markedly high biological activity was maintained by the modified sample prepared by using the compound of the present invention represented by formula (2) despite of the high degree of modification.

TABLE 1

| Activity of chemically modified G-CSF derivatives | |
| --- | --- |
| Sample name | Relative specific activity |
| G-CSF derivative modified with Compound 7 of Example 2 | 75 |
| G-CSF derivative of Reference Example 1 | 100 |
| Polyethylene glycol-modified G-CSF derivative of Reference Example 2 | 18 |

TEST EXAMPLE 2

Thermal Stability of Chemically Modified G-CSF Derivatives:

The unmodified G-CSF derivative and each of chemically modified G-CSF derivatives were adjusted to 0.2 mg/ml in 50 mmol/l phosphate buffer (pH 7.2), and changes in the circular dichroism polarization (CD) spectrum accompanied by the changes in temperature increase were measured. Changes in the spectrum value (ellipticity) at a wavelength of 208 nm are shown in FIG. 1. In the unmodified G-CSF derivative, rapid reduction and disappearance of the ellipticity (absolute value) were confirmed at 50 to 55° C., and this change was irreversible. On the other hand, similar to the case of the polyethylene glycol-modified sample, the ellipticity was almost constant until 55° C. in the inventive compound-modified G-CSF derivative, and the ellipticity (absolute value) was reduced just slightly even when the temperature was increased to 75° C. This result shows that the modified compound of the present invention is present and stably maintains the structure in the aqueous solution even when the temperature is increased.

TEST EXAMPLE 3

Solubility of Chemically Modified Low Molecular Compounds in Water

When solubility of the compounds prepared in Example 4 and Example 5 in water was measured, the results shown in Table 2 were obtained. Based on these results, it was found that solubility in water is improved when the compound prepared in Example 1 is bound to a hardly soluble low molecular compound.

TABLE 2

| Example | Compound No. | Saturated aqueous solution concentration (mol/l) |
|---|---|---|
| 4 | 26a | $0.65 \times 10^{-2}$ |
|  | 27a | 0.35 |
|  | 28a | >3.3 |
| 5 | 26b | 0.09 |
|  | 27b | 0.41 |
|  | 28b | >0.80 |

EXAMPLE 1

Synthesis of Compounds [Compounds Represented By Formula (2)]:

The reaction scheme is shown below. In the reaction scheme, Bn represents benzyl; Et represents ethyl; i-Pr represents isopropyl; PyBOP represents benzotriazol-1-yloxy-hris(pyrrolidino)phosphonium hexafluorophosphine; TFA represents trifluoroacetic acid; NHS represents N-hydroxysuccinimide; EDC represents 1-ethyl-3-(3-dimethylaminopropyl)carbodiimide hydrochloride; TBF represents tetrahydrofuran; and DMF represents dimethylformamide.

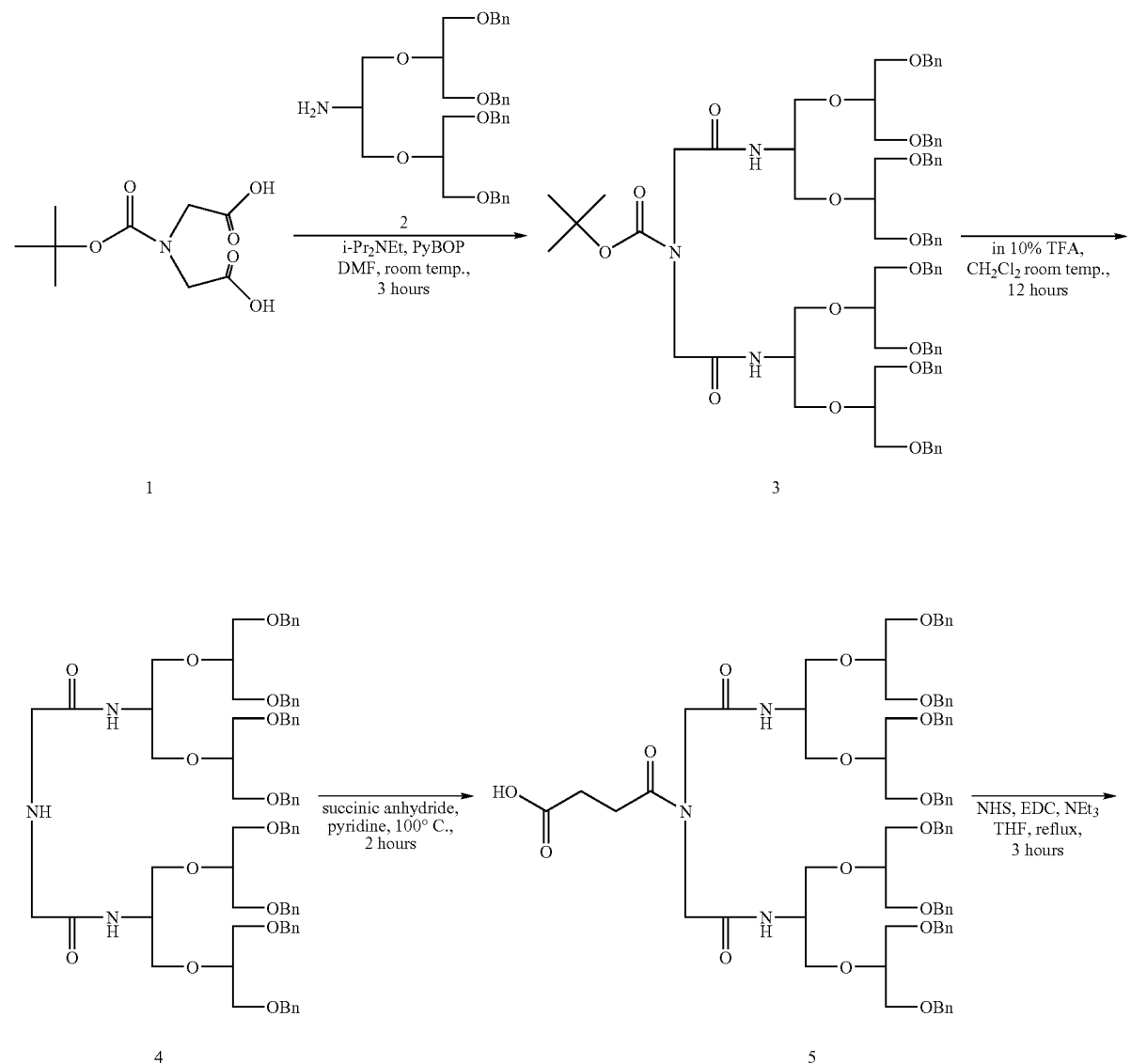

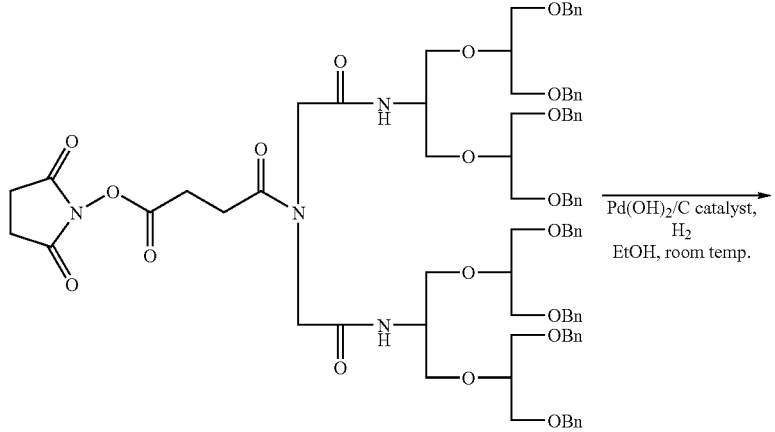

6

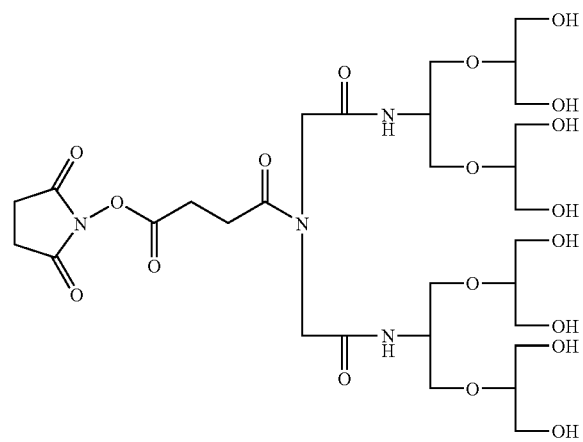

7

Compound 2 [2-amino-1,3-bis(1,3-di-O-benzyl-2-glyceroxy)propane] was prepared according to the method of Nemoto et al. [*J. Med. Chem.*, 38, 1673 (1995)]. Diisopropylethylamine (10.5 ml, 60.0 mmol), a DMF solution (20 ml) of Compound 2 (19.8 g, 33.0 mmol) and benzotriazol-1-yloxy-tris(pyrrolidino)phosphonium hexafluorophosphine (PyBOP; 15.6 g, 30.0 mmol) were added to a dimethylformamide (DMF) solution (50 ml) of Compound 1 (3.5 g, 15.0 mmol) in this order at room temperature, followed by stirring at the same temperature for 15 hours. The reaction solution was poured into 5% aqueous potassium hydrogensulfate solution, followed by extraction with ethyl acetate. The organic layer was washed with a saturated aqueous sodium hydrogencarbonate solution and a saturated brine in this order, dried over anhydrous magnesium sulfate and then filtered. The solvent was evaporated under reduced pressure, and the residue was purified by silica gel column chromatography (hexane:ethyl acetate=3:2) to give Compound 3 (18.7 g, yield 89%) as pale yellow oil.

$^1$H-NMR (CDCl$_3$, 300 MHz) δ (ppm): 1.36 (9H, s), 3.40-3.81 (32H, m), 4.16 (2H, m), 4.48 (16H, s), 7.19-7.31 (40H, m).

Trifluoroacetic acid (5 ml) was poured into a dichloromethane solution (45 ml) of Compound 3 (2.0 g, 1.43 mmol) at room temperature, followed by stirring at the same temperature for 20 hours. A saturated aqueous sodium hydrogencarbonate solution was added to the reaction solution, followed by extraction with dichloromethane. The organic layer was dried over anhydrous magnesium sulfate and filtered, and then the solvent was evaporated under reduced pressure to give Compound 4 (1.19 g, yield 64%) as pale yellow oil.

$^1$H-NMR (CDCl$_3$ 300 MHz) δ (ppm): 1.75 (1H, s), 2.87 (4H, s) 3.47-3.81 (28H, m), 4.16 (2H, m), 4.48 (16H, s), 7.00 (2H, d), 7.19-7.31 (40H, m).

Succinic anhydride (232 mg, 2.31 mmol) was gradually added to a pyridine solution (2.0 ml) of Compound 4 (1.5 g, 1.16 mmol) at room temperature, followed by stirring at 100° C. for 1.5 hours. The reaction solution was cooled to room temperature, and 2 mol/l hydrochloric acid was added thereto, followed by extraction with dichloromethane. The organic layer was washed with a saturated brine, dried over anhydrous magnesium sulfate and then filtered. The solvent was evaporated under reduced pressure, and the residue was purified by silica gel column chromatography (hexane:ethyl acetate=1:3) to give Compound 5 (1.62 g, yield 100%) as pale yellow oil.

$^1$H-NMR (CDCl$_3$, 300 MHz) δ (ppm): 2.39 (2H, m), 2.56 (2H, m), 3.45-3.76 (32H, m), 4.09-4.21 (2H, m), 4.46 (16H, s), 6.87 (1H, d), 7.19-7.31 (40H, m), 8.02 (1H, d).

N-hydroxysuccinimide (NHS; 495 mg, 4.30 mmol), 1-ethyl-3-(3-dimethylaminopropyl)carbodiimide hydrochloride (EDC; 886 mg, 4.30 mmol) and triethylamine (0.24 ml, 1.72 mmol) were added to tetrahydrofuran solution (45 ml) of Compound 5 (3.0 g, 2.15 mmol) in this order at room temperature, followed by refluxing for 2 hours. Then, 5% aqueous potassium hydrogensulfate solution was added thereto, followed by extraction with dichloromethane. The organic layer was washed with a saturated aqueous sodium hydrogencarbonate solution and a saturated brine in this order, dried over anhydrous magnesium sulfate and then filtered. The solvent was evaporated under reduced pressure, and the residue was purified by silica gel column chromatography (hexane:ethyl acetate=1:10) to give Compound 6 (2.35 g, yield 79%) as pale yellow oil.

$^1$H-NMR (CDCl$_3$, 300 MHz) δ (ppm): 2.49 (2H, t), 2.67 (4H, s), 2.78 (2H, t), 3.40-3.78 (32H, m), 4.11-4.22 (2H, m), 4.48 (16H, d), 6.96 (1H, d), 7.19-7.31 (40H, m), 8.37 (1H, d).

To an ethanol solution (50 ml) of Compound 6 (1.15 g, 0.77 mmol), Pd(OH)$_2$/C (Pd content: 20% by weight, 200 mg) was added under hydrogen stream at room temperature, followed by stirring at the same temperature for 12 hours. The reaction solution was filtered through celite, and then the solvent was evaporated under reduced pressure to give Compound 7 (596 mg, yield 100%) as pale yellow oil.

$^1$H-NMR (CDCl$_3$, 300 MHz) δ (ppm): 2.74 (2H, t), 2.82 (4H, s), 2.96 (2H, t), 3.30 (8H, s), 3.43-3.80 (28H, m), 4.05-4.22 (6H, m).

EXAMPLE 2

Preparation of Chemically Modified G-CSF Derivative Modified with the Compound of the Present Invention:

To the G-CSF derivative of Reference Example 1 (27.8 ml, 0.72 mg/ml) prepared by using an isotonic phosphate buffer (pH 7.4), Compound 7 prepared in Example 1 (about 20 mg) was added, followed by stirring for reaction a day and night under cooling. The reaction solution (26.5 ml) was diluted 10-fold with 20 mmol/l acetate buffer (pH 4.5) and purified by a cation exchange column using 10 ml of CM Sepharose FF resin (manufactured by Amersham-Pharmacia Biotech). The desired fraction eluted with a buffer containing 0.3 mol/l sodium chloride was recovered to obtain a solution containing 2.1 mg/ml of Compound 7-modified G-CSF derivative (8 ml, yield 84%).

<SDS-PAGE Analysis>

Analytical conditions:
  4 to 20% gradient gel (PAGEL SPG-520L), non-reducing
Result: A uniform band between 21 kDa and 31 kDa <Gel Filtration HPLC Analysis>

Analytical conditions:
  TSK gel G2000SW$_{XL}$ column (7.8×300 mm, manufactured by Tosoh), flow rate: 0.5 ml/min, solvent: 20 mmol/l sodium acetate buffer (pH 4.5) containing 150 mmol/l sodium chloride, injected amount; 50 μg
Result: Elution at about 19 minutes <MALDI TOF-MS Analysis>
Result: Masses 20880 (3 molecules-bound form) and 21540 (4 molecules-bound form) were mainly detected

EXAMPLE 3

Synthesis of Compounds [Compounds Represented By Formula (3)]:

The reaction scheme is shown below. In the reaction scheme, Bn represents benzyl.

1 + 4 ⟶

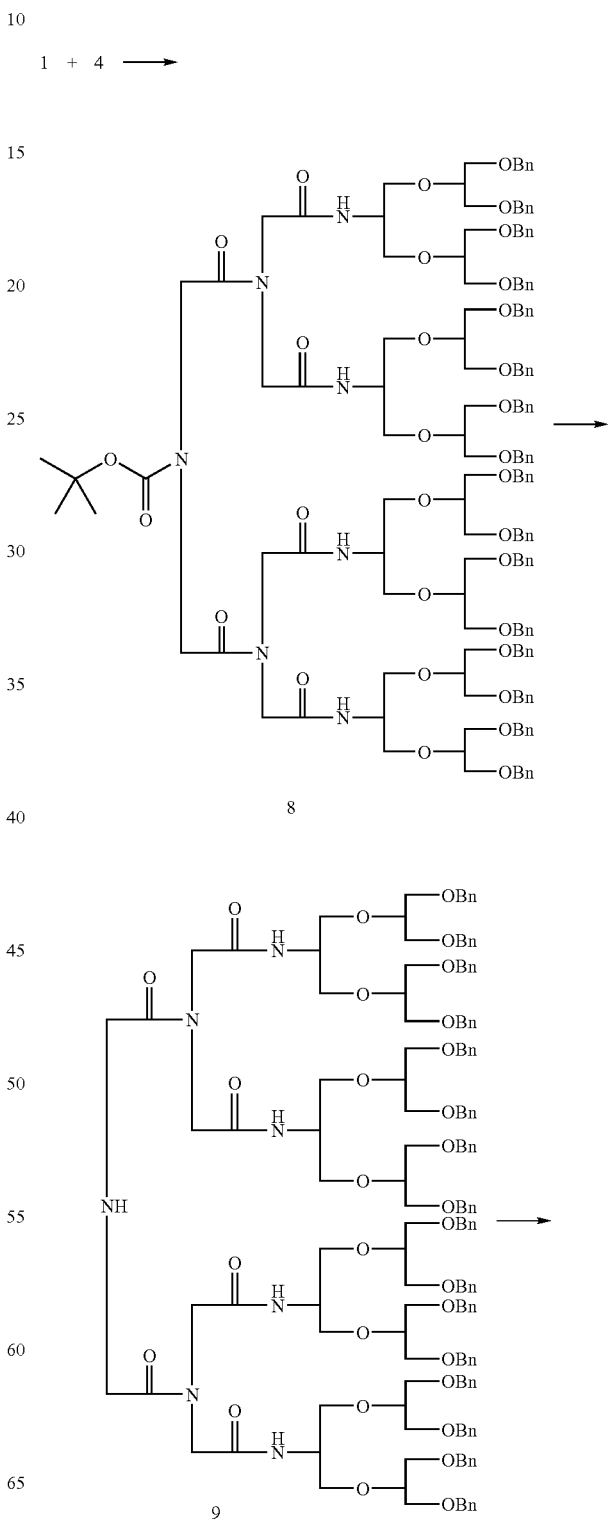

-continued

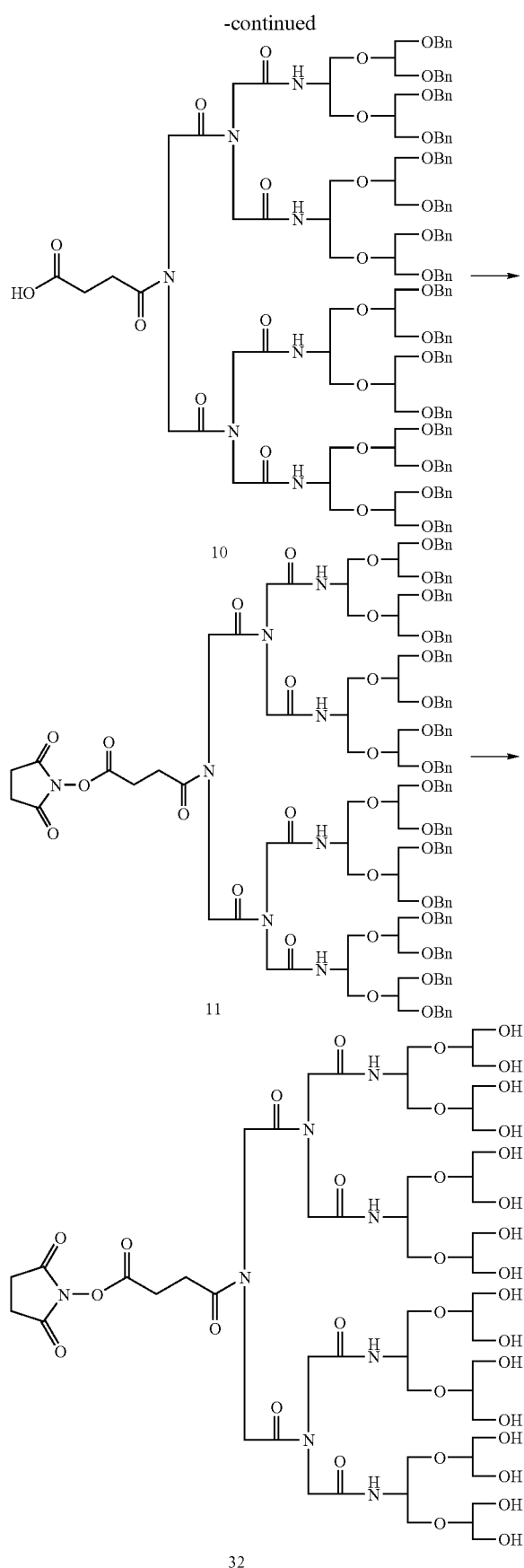

Compound 1 (51 mg, 0.219 mmol), diisopropylethylamine (0.15 ml, 0.876 mmol) and PyBOP (228 m, 0.428 mmol) were added to a DMF solution (13 ml) of Compound 4 (624 mg, 0.48 mmol) at room temperature, followed by stirring at the same temperature for 48 hours. The reaction mixture was poured into 5% aqueous potassium hydrogensulfate solution, followed by extraction with ethyl acetate, and the organic layer was washed with a saturated aqueous sodium hydrogencarbonate solution and a saturated brine in this order. Thereafter, the organic layer was dried over anhydrous magnesium sulfate and filtered, and then the solvent was evaporated under reduced pressure. The residue was purified by using silica gel column chromatography (ethyl acetate:acetic acid 100:0.7) to give Compound 8 (322 mg, 0.115 mmol) yield 53%) as yellow oil.

$^1$H-NMR (CDCl$_3$, 400 MHz) δ (ppm) 7.32-7.17 (80H, m), 4.49-4.38 (32H, m), 4.15-4.06 (4H, m), 3.77-3.27 (68H, m), 1.32 (9H, s), (CONH was not clearly identified).

$^{13}$C-NMR (CDCl$_3$, 75 MHz) δ (ppm): 170.2 (C×4, CONH), 167.7 (C×2, CON), 155.4 (C, O$_2$CN), 138.2 (C×16), 128.3 (CH×16), 128.3 (CH×16), 127.7 (CH×16), 127.6 (CH×16), 127.6 (CH×16), 80.5 (C), 78.7 (CH×8), 73.2 (CH$_2$×16), 70.2 (CH$_2$×16), 68.9 (CH$_2$×8), 52.1 (CH$_2$×2), 51.9 (CH$_2$×4), 49.6 (CH×4), 28.2 (CH$_3$×3).

Trifluoroacetic acid (0.48 ml) was added dropwise to a dichloromethane solution (48.32 ml) of Compound 8 (322 mg, 0.115 mmol) at room temperature. After stirring at the same temperature for 24 hours, the reaction solution was poured into a saturated aqueous sodium hydrogencarbonate solution, followed by extraction with dichloromethane, the organic layer was dried over anhydrous magnesium sulfate and filtered, and then the solvent was evaporated under reduced pressure to give Compound 9 (310 mg, 0.115 mmol, yield 100%) as white oil. This product was subjected to subsequent reaction without purification.

$^1$H-NMR (CDCl$_3$, 400 MHz) δ (ppm): 7.33-7.18 (80H, m), 4.50-4.39 (32H, m), 4.20-4.02 (4H, m), 3.94-3.28 (68H, m), (NH was not clearly identified), (CONH was not clearly identified).

Succinic anhydride (28 mg, 0.28 mmol) and N,N-dimethylaminopyridine (4 mg, 0.036 mmol) were added to a pyridine solution (3 ml) of Compound 9 (190 mg, 0.071 mmol) at room temperature, followed by stirring at 50° C. for 5 hours. The reaction solution was added to 2 mol/l aqueous hydrochloric acid solution, followed by extraction with dichloromethane. The organic layer was washed with a saturated brine, dried over anhydrous magnesium sulfate and filtered, and then the solvent was evaporated under reduced pressure. The residue was purified by using silica gel column chromatography (ethyl acetate:acetic acid=100:0.7) to give Compound 10 (150 mg, 0.054 mmol, yield 76%) as white oil.

$^1$H-NMR (CDCl$_3$, 400 MHz) δ (ppm): 7.35-7.17 (80H, m), 4.50-4.39 (32H, m), 4.22-4.05 (4H, m), 4.02-3.27 (68H, m), 2.62-2.53 (4H, m), (neither OH nor CONH was clearly identified).

NHS (12 mg, 0.11 mmol) was added to a tetrahydrofuran solution (2 ml) of Compound 10 (150 mg, 0.054 mmol) at room temperature, followed by stirring at the same temperature for 15 minutes, and then EDC (21 mg, 0.11 mmol) and triethylamine (7 ml, 0.043 mmol) were added thereto at room temperature, followed by refluxing for 30 minutes. The reaction solution was added to 5% aqueous KHSO$_4$ solution, followed by extraction with dichloromethane, the organic layer was washed with a saturated aqueous sodium hydrogencarbonate solution and a saturated brine in this order, dried over anhydrous magnesium sulfate and filtered, and then the solvent was evaporated under reduced pressure. The residue was purified by using flash column chromatography (ethyl acetate:hexane=20:1) to give Compound 11 (62 mg, 0.21 mmol, yield 40%) as oil.

$^1$H-NMR (CDCl$_3$, 400 MHz) δ (ppm): 7.39-7.18 (80H, m), 4.54-4.38 (32H, m), 4.23-4.07 (4H, m), 4.89-3.33 (68H, m), 2.77-2.69 (4H, m), 2.57-2.49 (4H, m), (CONH was not clearly identified).

$^{13}$C-NMR (CDCl$_3$, 75 MHz) δ (ppm); 172.1 (C, CO$_2$—), 170.4 (C, CON), 169.5 (C×4, CONH, 168.7 (C×2, CON), 168.1 (C×2, CON), 138.8 (C×16), 129.0 (CH×16), 129.0 (CH×16), 128.2 (CH×16), 128.0 (CH×16), 127.6 (CH×16), 79.3 (CH×8), 73.8 (CH$_2$×16), 70.5 (CH$_2$×16), 68.9 (CH$_2$×8), 52.1 (CH$_2$×2), 51.9 (CH$_2$×4), 50.4 (CH×4), 30.3 (CH$_2$), 30.2 (CH$_2$), 25.9 (CH$_2$×2).

TOF-MS: precision mass spectrometry (M)=2886, measured value (M+1)=2887.44

To an ethanol solution (1 ml) of Compound 11 (14 mg, 4.85 μmol), Pd(OH)$_2$/C (Pd content: 20% by weight, 1 mg) was added under hydrogen stream at room temperature, followed by stirring at the same temperature for 3 hours. The reaction solution was filtered through Celite 535, and then the solvent was evaporated under reduced pressure to give Compound 32 (6 mg 4.15 μmol, yield 86%).

$^1$H-NMR (CD$_3$OD, 400 MHz) δ (ppm): 4.27-4.07 (4H, m), 3.85-3.36 (72H, m), 2.66-2.41 (8H, m)

EXAMPLE 4

Synthesis of Chemically Modified Low Molecular Compounds (Compounds 24a to 28a) Modified with the Compound of the Present Invention:

The reaction scheme is shown below. In the reaction scheme, Et represents ethyl; Bn represents benzyl; NHS represents N-hydroxy succinimide; EDC represents 1-ethyl-3-(3-dimethylaminopropyl)carbodiimide hydrochloride; and THE represents tetrahydrofuran.

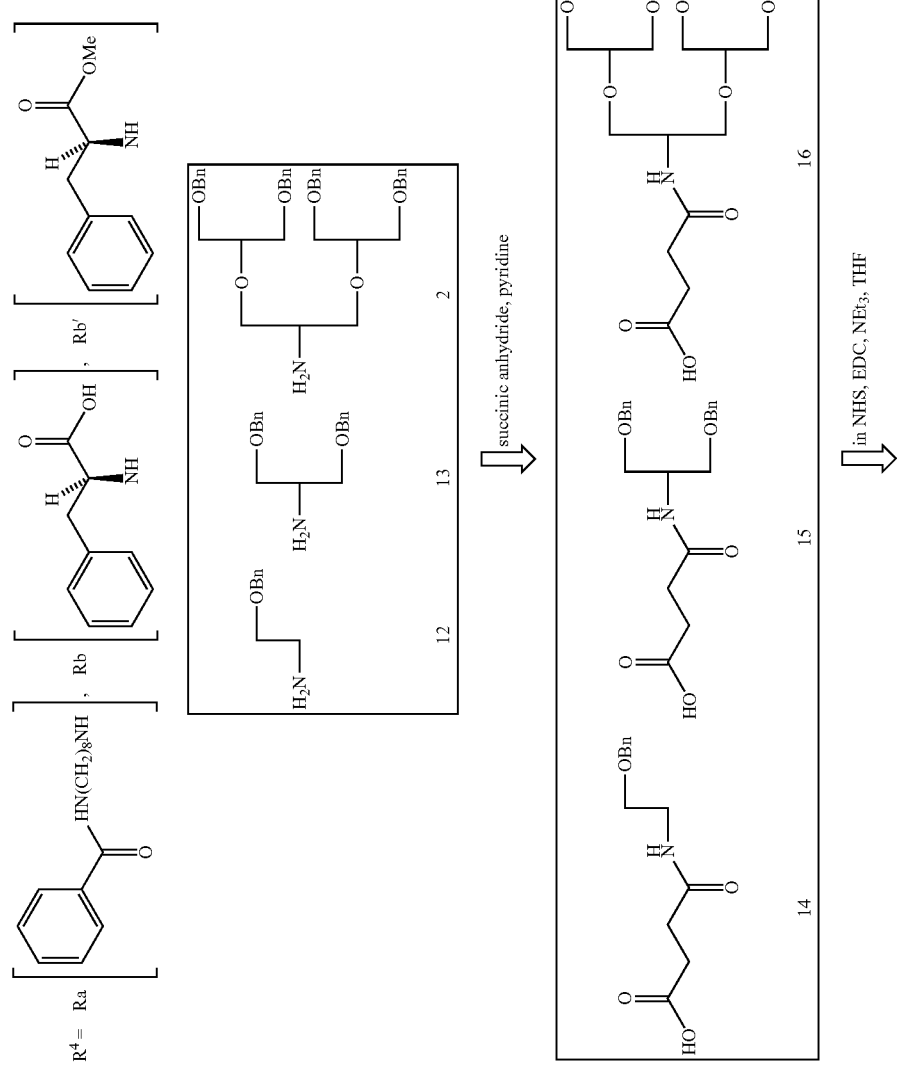

-continued
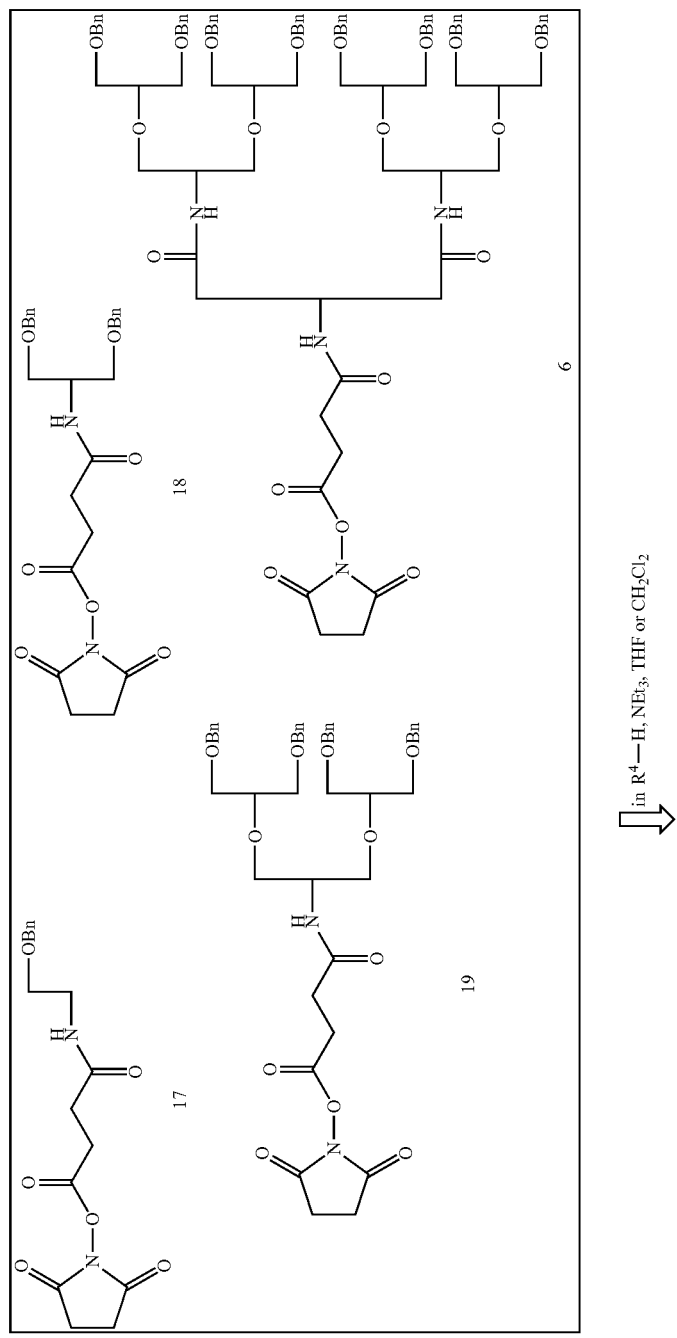

-continued
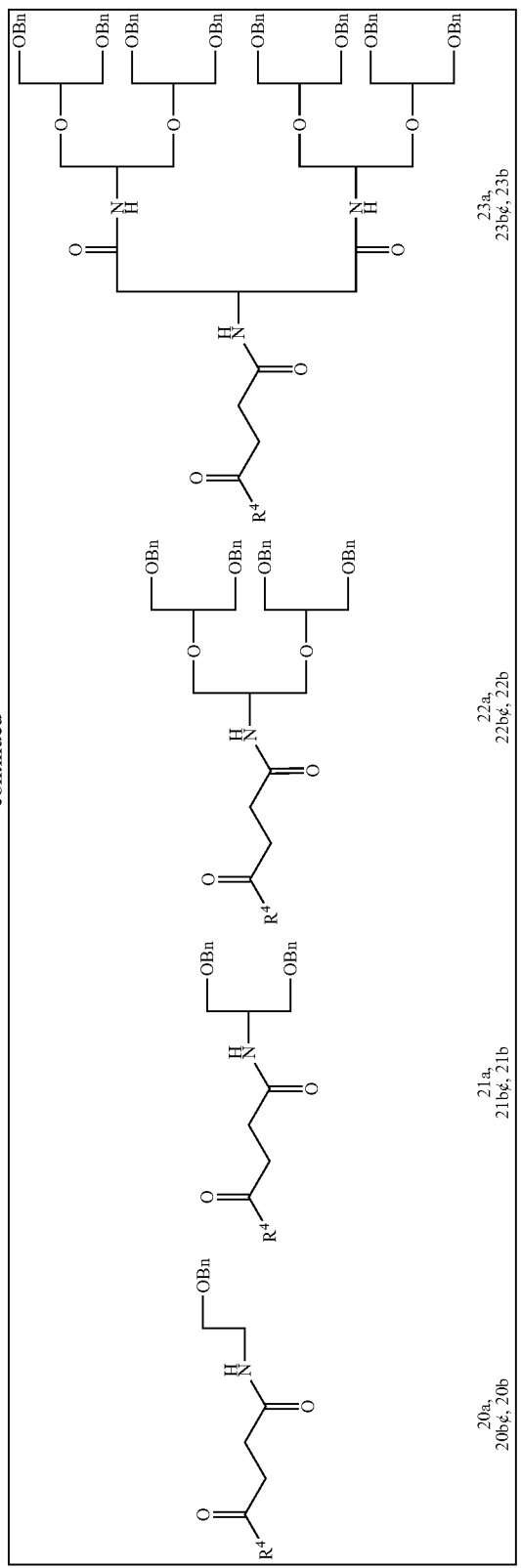
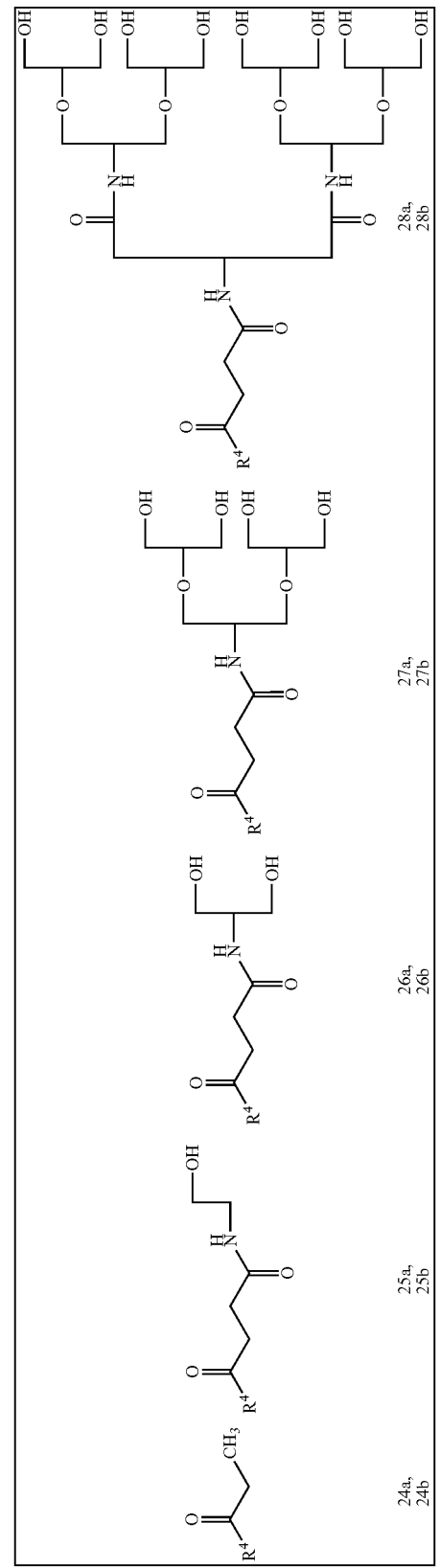

Compound 12 was synthesized by the method described in *Synth. Commun.*, 25, 907 (1995), and Compound 13 and Compound 2 were synthesized by the method described in *J. Med. Chem.*, 38, 1673 (1995).

Succinic anhydride (150.1 mg, 1.5 mmol) was gradually added to a pyridine solution (2.0 ml) of each of Compounds 12, 13 and 2 (1.0 mmol) at room temperature, followed by stirring at 100° C. for 1.5 to 4 hours, respectively. The reaction solution was cooled to room temperature, and 2 mol/l hydrochloric acid was added thereto, followed by extraction with dichloromethane. The organic layer was washed with a saturated brine, dried over anhydrous magnesium sulfate and then filtered. The solvent was evaporated under reduced pressure, and the residue was purified by silica gel column chromatography (hexane:ethyl acetate=1:3) to give each of Compounds 14 to 16, respectively (yield 92 to 100%).

(Compound 14)

$^1$H-NMR (CDCl$_3$, 400 MHz) δ (ppm): 2.51 (2H, t, J=7.0 Hz), 2.69 (2H, t, J=7.0 Hz), 3.49 (2H, t, J=5.0 Hz), 3.59 (2H, t, J=5.0 Hz), 4.54 (2H, s), 6.20 (1H, t, J=5.0 Hz), 7.31-7.42 (5H, m).

$^{13}$C-NMR (CDCl$_3$, 75 MHz) δ (ppm): 175.8 (C), 172.5 (C), 137.4 (C), 128.1 (CH×2), 127.5 (CH×2), 127.5 (CH), 72.6 (CH$_2$), 68.2 (CH$_2$), 39.1 (CH$_2$), 30.2 (CH$_2$), 29.2 (CH$_2$).

(Compound 15)

$^1$H-NMR (CDCl$_3$, 400 MHz) δ (ppm): 2.49 (2H, t, J=5.0 Hz), 2.57 (2H, t, J=5.0 Hz), 3.54 (2H, dd, J=7.2, 4.9 Hz), 3.64 (2H, dd, J=7.2, 3.0 Hz), 4.25-4.32 (1H, m), 4.50 (4H, s), 6.09 (1H, d, J=6.9 Hz), 7.25-7.37 (10H, m).

$^{13}$C-NMR (CDCl$_3$, 75 MHz) δ (ppm): 175.8 (C), 171.6 (C), 137.7 (C×2), 128.3 (CH×4), 127.6 (CH×4), 127.6 (CH×2), 127.6 (C), 73.1 (CH$_2$×2), 68.3 (CH$_2$×2), 48.7 (CH), 30.6 (CH$_2$), 29.6 (CH$_2$).

(Compound 16)

$^1$H-NMR (CDCl$_3$, 400 MHz) δ (ppm): 2.06 (2H, t, J=5.0 Hz), 2.44 (2H, t, J=5.0 Hz), 3.50-3.82 (14H, m), 4.09-4.16 (1H, m), 4.50 (2H, s), 4.50 (2H, s), 6.82 (1H, d, J=6.5 Hz), 7.25-7.36 (20H, m).

$^{13}$C-NMR (CDCl$_3$, 300 MHz) δ (ppm): 175.3 (C), 172.0 (C), 137.9 (C×2), 137.7 (C×2), 128.2 (CH×4), 128.2 (CH×4), 127.7 (CH×4), 127.6 (CH×4), 127.5 (CH×2), 127.4 (CH×2), 78.9 (CH×2), 73.4 (CH$_2$×2), 73.2 (CH$_2$×2), 70.5 (CH$_2$×2), 69.9 (CH$_2$×2), 68.4 (CH$_2$×2), 49.6 (CH), 30.1 (CH$_2$), 30.0 (CH$_2$).

NHS (126.6 mg, 1.1 mmol), EDC (412.7 mg, 2.0 mmol) and triethylamine (0.11 ml, 0.8 mmol) were added to a tetrahydrofuran solution (45 ml) of each of Compounds 14 to 16 (1.0 mmol) in this order at room temperature, followed by refluxing for 2 to 4 hours. Then, 5% aqueous potassium hydrogensulfate solution was added to the reaction solution, followed by extraction with dichloromethane. The organic layer was washed with a saturated aqueous sodium hydrogencarbonate solution and a saturated brine in this order, dried over anhydrous magnesium sulfate and then filtered The solvent was evaporated under reduced pressure, and the residue was purified by silica gel column chromatography (hexane:ethyl acetate=1:10) to give Compounds 17 to 19, respectively (yield 53 to 90%).

(Compound 17)

$^1$H-NMR (CDCl$_3$, 400 MHz) δ (ppm): 2.61 (2H, t, J=7.0 Hz), 2.87 (4H, s), 3.19 (2H, t, J=7.0Hz), 3.49 (2H, t, J=5.0 Hz), 3.59 (2H, t, J=5.0 Hz), 4.55 (2H, s), 6.13-6.25 (1H, m), 7.31-7.42 (5H, m).

$^{13}$C-NMR (CDCl$_3$, 75 MHz) δ (ppm): 170.1 (C×2), 169.1 (C), 168.2 (C), 137.8 (C), 128.5 (CH×2), 127.9 (CH××2), 127.9 (CH), 73.2 (CH$_2$), 68.9 (CH$_2$), 39.5 (CH$_2$), 30.6 (CH$_2$), 26.8 (CH$_2$), 25.5 (CH$_2$×2).

(Compound 18)

$^1$H-NMR (CDCl$_3$, 400 MHz) δ (ppm): 2.59 (2H, t, J=5.5 Hz), 2.79 (4H, s), 2.98 (2H, t, J=5.5 Hz), 3.54 (2H, dd, J=7.5, 5.0 Hz), 3.64 (2H, dd, J=7.5, 3.0 Hz), 4.27-4.34 (1H, m), 4.51 (4H, s), 5.95 (1H, d, J=6.8 Hz), 7.25-7.39 (10H, m). $^{13}$C-NMR (CDCl$_3$, 75 MHz) δ (ppm): 169.3 (C), 168.7 (C×2), 167.9 (C), 137.9 (C×2), 128.2 (CH×4), 127.6 (CH×4), 127.5 (CH×2), 73.1 (CH$_2$×2), 68.3 (CH$_2$×2), 48.6 (CH), 30.7 (CH$_2$), 26.7 (CH$_2$), 25.5 (CH$_2$×2).

(Compound 19)

$^1$H-NMR (CDCl$_3$, 400 MHz) δ (ppm): 2.12 (2H, t, J=5.8 Hz), 2.77-2.82 (6H, m), 3.51-3.82 (14H, m), 4.09-4.17 (1H, m), 4.50 (2H, s), 4.51 (2H, s), 6.68 (1H, d, J=7.0 Hz), 7.27-7.35 (20H, m).

$^{13}$C-NMR (CDCl$_3$, 75 MHz) δ (ppm): 169.2 (C), 68.7 (C×2), 167.8 (C), 138.0 (C×2), 137.8 (C×2), 128.3 (CH×4), 128.2 (CH×4), 127.7 (CH×4), 127.6 (CH×4), 127.4 (CH×4), 79.0 (CH×2), 73.4 (CH$_2$×2), 73.3 (CH$_2$×2), 70.6 (CH$_2$×2), 70.0 (CH$_2$×2), 68.5 (CH$_2$×2), 49.4 (CH), 29.8 (CH$_2$), 26.5 (CH$_2$), 25.0 (CH$_2$×2).

N-(8-aminooctyl)benzamide hydrochloride (compound Ra-H.HCl) was synthesized by the method described in *Synthesis*, 917 (1988).

Compound Ra-H.HCl (284.8 mg, 1.0 mmol) and triethylamine (0.14 ml, 1.0 mmol) were added to a tetrahydrofuran solution (20 ml) of each of Compounds 17 to 19 and 6 (1.0 mmol) in this order at room temperature, followed by stirring at the same temperature for 3 to 6 hours. Then, 5% aqueous potassium hydrogensulfate solution was added to the reaction solution, followed by extraction with chloroform. The organic layer was washed with a saturated aqueous sodium hydrogencarbonate solution and a saturated brine in this order, dried over anhydrous magnesium sulfate and then filtered. The solvent was evaporated under reduced pressure, and the residue was purified by silica gel column chromatography (CHCl$_3$:methanol=20:1) to give Compounds 20a to 23a, respectively (yield 62 to 79%).

(Compound 20a)

$^1$H-NMR (CDCl$_3$, 400 MHz) δ (ppm): 1.23-1.68 (12H, m), 2.46-2.65 (4H, m), 3.18-3.60 (8H, m), 4.51 (2H, s), 6.13-6.38 (3H, m), 7.30-7.86 (10H, m).

$^{13}$C-NMR (CDCl$_3$:CD$_3$OD=10:1, 75 MHz) δ (ppm): 172.9 (C), 172.7 (C), 168.1 (C), 137.8 (C), 134.7 (C), 131.5 (CH), 128.6 (CH×2), 128.5 (CH×2), 127.9 (CH×2), 127.9 (CH×2), 126.9 (CH), 73.2 (CH$_2$), 68.7 (CH$_2$), 40.0 (CH$_2$), 39.5 (CH$_2$), 39.4 (CH$_2$), 31.8 (CH$_2$), 31.7 (CH$_2$), 29.5 (CH$_2$), 29.2 (CH$_2$), 29.1 (CH$_2$), 29.0 (CH$_2$), 26.8 (CH$_2$), 26.7 (CH$_2$).

(Compound 21a)

$^1$H-NMR (CDCl$_3$, 400 MHz) δ (ppm): 1.23-1.68 (12H, m), 2.46-2.65 (4H, m), 3.20 (2H, q, J=5.0 Hz), 3.45 (2H, q, J=5.0 Hz), 3.52-3.66 (2H, dd, J=8.0, 4.5 Hz), 3.63 (2H, dd, J=8.0, 3.0 Hz), 4.23-4.31 (1H, m), 4.51 (4H, s), 5.94-6.19 (3H, m), 7.28-7.79 (15H, m).

$^{13}$C-NMR (CDCl$_3$, 75 MHz) δ (ppm): 172.1 (C), 172.0 (C), 167.6 (C), 137.8 (C×2), 134.6 (C), 131.2 (CH), 128.4 (CH×2), 128.3 (CH×6), 127.6 (CH×2), 127.5 (CH×2), 126.7 (CH×2), 73.1 (CH$_2$×2), 68.4 (CH$_2$×2), 48.6 (CH), 40.0 (CH$_2$), 39.5 (CH$_2$), 31.9 (CH$_2$), 31.8 (CH$_2$), 29.5 (CH$_2$), 29.3 (CH$_2$), 29.0 (CH2), 29.0 (CH$_2$), 26.8 (CH$_2$), 26.6 (CH$_2$).

(Compound 22a)

¹H-NMR (CDCl₃, 400 MHz) δ (ppm): 1.23-1.68 (12H, m), 2.17 (2H, t, J=5.0 Hz), 2.34 (2H, t, J=5.0 Hz), 3.15 (2H, q, J=5.0 Hz), 3.42 (2H, q, J=5.0 Hz), 3.52-3.65 (10H, m), 3.65-3.84 (4H, m), 4.07-4.15 (1H, m), 4.45 (4H, s), 4.50 (4H, s), 6.30-6.45 (2H, m), 6.73 (1H, d, J=6.0 Hz), 7.28-7.79 (25H, m).

¹³C-NMR (CDCl₃, 75 MHz) δ (ppm): 172.1 (C), 172.0 (C), 167.5 (C), 138.1 (C×2), 138.0 (C×2), 134.8 (C), 131.6 (CH), 128.4 (CH×2), 128.4 (CH×4), 128.3 (CH×4), 127.7 (CH×4), 127.7 (CH×2), 127.6 (CH×2), 127.6 (CH×4), 126.9 (CH×2), 79.0 (CH×2), 73.4 (CH₂×2), 73.3 (CH₂×2), 70.5 (CH₂), 70.4 (CH₂), 70.0 (CH₂), 70.0 (CH₂), 68.5 (CH₂×2), 49.4 (CH), 40.0 (CH₂), 39.4 (CH₂), 31.7 (CH₂), 31.4 (CH₂), 29.5 (CH), 29.4 (CH₂), 29.1 (CH₂), 29.0 (CH₂), 26.8 (CH₂), 26.7 (CH₂).

(Compound 23a)

¹H-NMR (CDCl₃, 400 MHz) δ (ppm): 1.23-1.68 (12H, m), 2.30 (2H, t, J=5.0 Hz), 2.45 (2H, t, J=5.0 Hz), 3.10 (2H, q, J=5.0 Hz), 3.40 (2H, q, J=5.0 Hz), 3.40-3.80 (32H, m), 4.10-4.22 (2H, m), 4.50 (16H, s), 5.87 (1H, brd, J=5.0 Hz), 6.32 (1H, brd, J=5.0 Hz), 7.08 (1H, d, J=6.0 Hz), 7.21-7.41 (40H, m), 7.41-7.55 (3H, m), 7.77 (2H, d, J=5.5 Hz), 8.29 (1H, d, J=6.0 Hz).

¹³C-NMR (CDCl₃, 75 MHz) δ (ppm): 173.1 (C), 171.7 (C), 168.5 (C), 168.0 (C), 167.3 (C), 138.1 (C×2), 138.0 (C×4), 137.9 (C×2), 134.7 (C), 131.1 (CH), 128.3, 128.2, 128.2, 127.6, 127.6, 127.5, 127.5, 127.5, 127.4, 127.4, and 126.7 (CH×44), 78.9 (CH×2), 78.8 (CH×2), 73.3 (CH₂×2), 73.3 (CH₂×2), 73.2 (CH₂×4), 70.3 (CH₂×2), 70.2 (CH₂×2), 69.9 (CH₂×2), 69.9 (CH₂×2), 68.8 (CH₂×2), 68.3 (CH₂×2), 53.4 (CH₂), 52.3 (CH₂), 49.9 (CH), 49.6 (CH), 40.0 (CH₂), 39.4 (CH₂), 31.1 (CH₂), 29.5 (CH₂), 29.4 (CH₂), 29.1 (CH₂), 29.0 (CH₂), 28.2 (CH₂), 26.8 (CH₂), 26.7 (CH₂).

To an ethanol solution (15 ml) of each of Compounds 20a to 23a (1.0 mmol), catalytic amount of Pd(OH)OC (Pd content: 20% by weight) was added under hydrogen stream at room temperature, followed by stirring at the same temperature for 3 to 6 hours. The reaction solution was filtered through Celite 535 (manufactured by Wako Pure Chemical Industries), and then the solvent was evaporated under reduced pressure to give Compounds 25a to 28a, respectively (yield 100%).

(Compound 25a)

¹H-NMR (CD₃OD, 400 MHz) δ (ppm): 1.28-1.41 (8H, m), 1.45-1.52 (2H, m), 1.58-1.66 (2H, m), 2.46-2.50 (4H, m), 3.16 (2H, t, J=5.5 Hz), 3.30 (2H, t, J=4.5 Hz), 3.38 (2H, t, J=5.5 Hz), 3.58 (2H, t, J=4.5 Hz), 7.41-7.53 (3H, m), 7.77-7.81 (2H, m).

¹³C-NMR (CDCl₃:CD₃OD=1:10, 75 MHz) δ (ppm): 174.7 (C), 174.3 (C), 170.1 (C), 135.6 (C), 132.3 (CH), 129.3 (CH×2), 128.0 (CH×2), 61.4 (CH₂), 42.8 (CH₂), 40.9 (CH₂), 40.3 (CH₂), 32.2 (CH₂), 32.1 (CH₂), 30.3 (CH₂), 30.2 (CH₂), 30.2 (CH₂×2), 27.8 (CH₂), 27.7 (CH₂).

(Compound 26a)

¹H-NMR (CD3OD, 400 MHz) δ (ppm): 1.28-1.41 (8H, m), 1.45-1.52 (2H, m), 1.58-1.66 (2H, m), 2.46-2.52 (4H, m), 3.16 (2H, t, J=5.5 Hz), 3.38 (2H, t, J=5.5 Hz), 3.55-3.65 (4H, m), 3.90 (1H, q, J=4.0 Hz), 7.41-7.53 (3H, m), 7.77-7.81 (2H, m).

¹³C-NMR (CDCl₃:CD₃OD=3:7, 75 MHz) δ (ppm): 173.9 (C), 173.4 (C), 169.2 (C), 134.9 (C), 131.8 (CH), 128.8 (CH×2), 127.4 (CH×2), 61.6 (CH₂×2), 53.3 (CH), 40.4 (CH₂), 39.8 (CH₂), 31.9 (CH₂), 31.6 (CH₂), 29.7 (CH₂), 29.5 (CH₂×3), 27.2 (CH₂), 27.1 (CH₂).

(Compound 27a)

¹H-NMR (CD₃OD, 400 MHz) δ (ppm): 1.28-1.41 (8H, m), 1.45-1.52 (2H, m), 1.58-1.66 (2H, m), 2.46-2.52 (4H, m), 3.16 (2H, t, J=5.0 Hz), 3.35 (2H, t, J=5.0 Hz), 3.55-3.80 (14H, m), 4.07-4.15 (1H, m), 7.41-7.53 (3H, m), 7.77-7.81 (2H, m).

¹³C-NMR (CD3OD, 75 MHz) δ (ppm): 174.5 (C), 174.3 (C), 169.9 (C), 135.7 (C), 132.4 (CH), 129.4 (CH×2), 128.1 (CH×2), 82.9 (CH×2), 69.5 (CH₂×2), 62.4 (CH₂×2), 62.3 (CH₂×2), 51.0 (CH), 40.9 (CH₂), 40.5 (CH₂), 32.3 (CH₂), 32.2 (CH₂), 30.4 (CH₂×2), 30.2 (CH₂×2), 27.9 (CH₂), 27.8 (CH₂).

(Compound 28a)

¹H-NMR (CD₃OD, 400 MHz) δ (ppm): 1.28-1.41 (8H, m), 1.45-1.52 (2H, m), 1.58-1.66 (2H, m), 2.48 (2H, t, J=5.0 Hz), 2.60 (2H, t, J=5.0 Hz), 3.16 (2H, t, J=5.5 Hz), 3.38 (2H, t, J=5.5 Hz), 3.52-3.82 (28H, m), 4.05 (2H, s), 4.15 (1H, t, J=4.0 Hz), 4.22 (1H, t, J=4.0 Hz), 4.27 (2H, s), 7.41-7.53 (3H, m), 7.77-7.81 (2H, m).

¹³C-NMR (CD₃OD, 75 MHz) δ (ppm): 175.6 (C), 174.2 (C), 171.7 (C), 171.4 (C), 170.0 (C), 135.7 (C), 132.4 (CH), 129.4 (CH×2), 128.1 (CH×2), 83.1 (CH×2), 82.9 (CH×2), 69.7 (CH₂×2), 69.5 (CH₂×2), 62.6 (CH₂×2), 62.5 (CH₂×2), 62.4 (CH₂×4), 54.5 (CH₂), 54.0 (CH₂), 51.6 (CH), 51.3 (CH), 41.0 (CH₂), 40.5 (CH₂), 31.7 (CH₂), 30.5 (CH₂), 30.3 (CH₂×2), 30.3 (CH₂), 29.2 (CH₂), 28.0 (CH₂), 27.9 (CH₂).

The reaction was carried out in the same manner as in the above using Ra-H.HCl and NHS ester of propionic acid to give Compound 24a (N-(8-propionylaminooctyl)benzamide).

¹H-NMR (CDCl₃, 400 MHz) δ (ppm): 1.15 (3H, t, J=6.0 Hz), 1.29-1.68 (12H, m), 2.19 (2H, q, J=5.0 Hz), 3.22 (2H, q, J=5.0 Hz), 3.44 (2 H, q, J=5.0 Hz), 5.71 (1H, brd, CONH), 6.38 (1H, brd, CONH, 7.40-7.50 (3H, m), 7.77 (2H, d, J=6.0 Hz).

¹³C-NMR (CDCl₃, 75 MHz) δ (ppm): 174.0 (C), 167.6 (C), 134.8 (C), 131.3 (CH), 128.5 (CH×2), 126.9 (CH×2), 40.0 (CH₂), 39.5 (CH₂), 29.7 (CH₂), 29.6 (CH₂), 29.5 (CH₂), 29.0 (CH₂), 29.0 (CH₂), 26.8 (CH₂), 26.7 (CH₂), 10.0 (CH₃).

EXAMPLE 5

Synthesis of Compounds (Compounds 24b to 28b):

L-phenylalanine methyl ester hydrochloride (compound Rb'-H.HCl, 431.4 mg, 2.0 mmol) and triethylamine (0.42 ml, 3.0 mmol) were added to a dichloromethane solution (20 ml) of each of Compounds 17 to 19 and 6 (1.0 mmol) in this order at room temperature, followed by stirring at the same temperature for 3 to 6 hours. Then, 5% aqueous potassium hydrogensulfate solution was added to the reaction solution, followed by extraction with dichloromethane. The organic layer was washed with a saturated aqueous sodium hydrogencarbonate solution and a saturated brine in this order, dried over anhydrous magnesium sulfate and then filtered. The solvent was evaporated under reduced pressure, and the residue was purified by silica gel column chromatography (hexane:ethyl acetate=1:3) to give Compounds 20b' to 23b' respectively (yield 79 to 97%).

(Compound 20b')

¹H-NMR (CDCl₃, 400 MHz) δ (ppm): 2.40 (2H, t, J=5.0 Hz), 2.49 (2H, t, J=5.0 Hz), 2.98 (1H, dd, J=11.0, 5.0 Hz), 3.09 (1H, dd, J=11.0, 5.0 Hz), 3.40 (2H, t, J=4.0 Hz), 3.48 (2H, t, J=4.0 Hz), 3.60 (3H, s), 4.45 (2H, s), 4.79 (1H, brq, J=5.0 Hz), 6.83 (1H, t, J=4.0 Hz), 7.10-7.32 (10H, m), (two —NHs were not clearly identified).

¹³C-NMR (CDCl₃, 75 MHz) δ (ppm): 171.0 (C), 170.9 (C), 170.9 (C), 136.8 (C), 135.1 (C), 128.0 (CH×2), 127.3 (CH×2), 127.2 (CH×2), 126.5 (CH×2), 125.7 (CH×2), 71.8 (CH₂), 67.7 (CH₂), 52.4 (CH₃), 51.0 (CH), 38.3 (CH₂), 36.7 (CH₂), 30.2 (CH₂×2).

(Compound 21b')

¹H-NMR (CDCl₃, 400 MHz) δ (ppm): 2.42-2.52 (4H, m), 3.05 (1H, dd, J=11.0, 5.0 Hz), 3.12 (1H, dd, J=11.0, 4.8 Hz), 3.52 (2H, dd, J=7.5, 4.5 Hz), 3.63 (2H, dd, J=7.5, 3.0 Hz), 3.70 (3H, s), 4.25-4.32 (1H, m), 4.50 (4H, s), 4.83 (1H, dt, J=6.0, 5.0 Hz), 6.06 (1H, d, J=6.0 Hz), 6.33 (1H, d, J=6.0 Hz), 7.08-7.35 (15H, m).

¹³C-NMR (CDCl₃, 75 MHz) δ (ppm): 172.0 (C), 171.7 (C), 171.7 (C), 138.0 (C×2), 136.0 (C), 129.2, 128.5, 128.4, 127.6 and 127.0 (CH×15), 73.1 (CH₂×2), 68.4 (CH₂×2), 53.3 (CH₃), 52.2 (CH), 48.6 (CH), 37.8 (CH₂), 31.4 (CH₂), 31.3 (CH₂).

(Compound 22b')

¹H-NMR (CDCl₃, 400 MHz) δ (ppm): 2.13 (2H, t, J=5.0 Hz), 2.34 (2H, t, J=5.0 Hz), 3.03 (1H, dd, J=11.0, 4.8 Hz), 3.11 (1H, dd, J=11.0, 4.8 Hz), 3.49-3.80 (14H, m), 3.67 (3H, s), 4.12 (1H, q, J=5.5 Hz), 4.49 (4H, s), 4.50 (4H, s), 4.80 (1H, dt, J=5.0, 6.0 Hz), 6.59-6.64 (2H, m), 7.09-7.33 (25H, m).

¹³C-NMR (CDCl₃, 100 MHz) δ (ppm): 171.9 (C), 171.7 (C), 171.6 (C), 138.1 (C×2), 138.0 (C×2), 136.0 (C), 129.2, 128.5, 128.4, 128.3, 127.7, 127.7, 127.6 and 127.0 (CH×25), 79.0 (CH), 79.0 (CH), 73.4 (CH₂×2), 73.3 (CH₂×2), 70.4 (CH₂), 70.0 (CH₂), 68.5 (CH₂×2), 68.5 (CH₂×2), 53.3 (CH₃), 52.1 (CH), 49.4 (CH), 37.8 (CH₂), 31.3 (CH₂), 30.9 (CH₂).

(Compound 23b')

¹H-NMR (CDCl₃, 400 MHz) δ (ppm): 2.26-2.45 (4H, m), 3.00 (1H, dd, J=11.0, 5.0 Hz), 3.06 (1H, dd, J=11.0, 5.0 Hz), 3.34-3.80 (32H, m), 3.63 (3H, s), 4.07-4.14 (1H, m), 4.17-4.25 (1H, m), 4.46 (16H, s), 4.77 (1H, dt, J=6.0, 5.0 Hz), 6.15 (1H, d, J=6.0 Hz), 6.97 (1H, d, J=7.0 Hz), 7.06-7.52 (45H, m), 8.36 (1H, d, J=6.0 Hz).

¹³C-NMR (CDCl₃, 100 MHz) δ (ppm): 173.0 (C), 171.8 (C), 171.5 (C), 168.8 (C), 168.3 (C), 138.3 (C×2), 138.2 (C×2), 138.2 (C×2), 138.1 (C×2), 136.0 (C), 129.3, 128.5, 128.4, 128.4, 127.8, 127.7, 127.6 and 127.0 (CH×45), 79.0 (CH×2), 78.6 (CH×2), 73.4 (CH₂×2), 73.3 (CH₂×2), 73.3 (CH₂×4), 70.4 (CH₂×2); 70.2 (CH₂×2), 70.0 (CH₂×2), 70.0 (CH₂×2), 68.9 (CH₂×2), 68.4 (CH₂×2), 53.6 (CH₂), 53.2 (CH₃), 52.3 (CH₂), 52.1 (CH), 49.9 (CH), 49.6 (CH) 37.8 (CH₂), 30.7 (CH₂), 27.8 (CH₂).

Each of Compounds 20b' to 23b' (1.0 mmol) was stirred in 10% potassium hydroxide ethanol solution (15 ml) at room temperature for 6 to 12 hours. Then, 5% aqueous potassium hydrogensulfate solution was added to the reaction solution, followed by extraction with ethyl acetate. The organic layer was washed with a saturated brine, dried over anhydrous magnesium sulfate and then filtered. The solvent was evaporated under reduced pressure to give Compounds 20b to 23b, respectively (yield 91 to 99%).

(Compound 20b)

¹H-NMR (CDCl₃, 400 MHz) δ (ppm): 2.43-2.49 (4H, m), 3.02 (1H, dd, J=11.0, 5.0 Hz), 3.16 (1H, dd, J=1.0, 4.0 Hz), 3.43 (2H, brt, J=3.5 Hz), 3.53 (2H, t, J=3.5 Hz), 4.50 (2H, s), 4.74 (1H, brdd, J=5.0, 4.0 Hz), 6.64 (1H, brd, CONH), 6.84 (1H, brd, J=3.5 Hz, CONH), 7.14-7.40 (10H, m), 8.45 (1H, brd, COOH).

¹³C-NMR (CDCl₃, 75 MHz) δ (ppm): 173.2 (C), 173.0 (C), 72.3 (C), 137.5 (C), 136.1 (C), 129.3 (CH), 128.3 (CH×2), 128.2 (CH×2), 127.7 (CH×2), 127.7 (CH×2), 126.6 (CH), 73.0 (CH₂), 68.4 (CH₂), 53.6 (CH), 39.5 (CH₂), 37.3 (CH₂), 31.8 (CH₂×2).

(Compound 21b)

¹H-NMR (CDCl₃, 400 MHz) δ (ppm): 2.40-2.46 (4H, m), 3.05 (1H, dd, J=11.0, 4.5Hz), 3.19 (1H, dd, J=11.0, 4.0 Hz), 3.51 (2H, dd, J=7.0, 4.5 Hz), 3.61 (2H, dd, J=7.0, 4.5 Hz), 4.20-4.28 (1H, m), 4.49 (4H, s), 4.72 (1H, ddd, J=6.0, 4.0, 4.5 Hz), 6.29 (1H, d, J=6.0 Hz CONH), 6.68 (1H, d, J=6.0 Hz, CONH), 7.12-7.36 (15H, m), (COOH was not clearly identified).

¹³C-NMR (CDCl₃, 75 MHz) δ (ppm): 173.5 (C), 172.9 (C), 172.3 (C), 137.8 (C×2), 136.2 (C),129.5, 129.5, 128.4, 128.4, 127.8, 127.8, 127.7 and 126.9 (CH×15), 73.2 (CH₂×2), 68.3 (CH₂×2), 53.5 (CH), 48.9 (CH), 37.3 (CH₂), 32.1 (CH₂), 32.0 (CH₂).

(Compound 22b)

¹H-NMR (CDCl₃, 400 MHz) δ (ppm); 2.14-2.41 (4H, m), 3.03 (1H, dd, J=11.0, 5.5 Hz), 3.18 (1H, dd, J=11.0, 4.5 Hz), 3.47-3.76 (14H, m), 4.07-4.13 (1H, m), 4.48-4.52 (8H, m), 4.67 (1H, brdd, J=5.5, 4.5 Hz), 6.76-6.86 (2H, m), 7.13-7.34 (25H, m), (COOH was not clearly identified).

¹³C-NMR (CDCl₃, 75 MHz) δ (ppm): 173.3 (C), 172.7 (C), 172.2 (C), 138.0 (C), 138.0 (C), 137.9 (C), 137.8 (C), 136.4 (C), 129.5, 128.4, 128.4, 128.3, 127.9, 127.8, 127.8, 127.7, 127.7, 127.7, 127.6 and 126.9 (CH×25), 79.0 (CH), 78.9 (CH), 73.4 (CH₂×2), 73.4 (CH₂×2), 70.3 (CH₂), 70.0 (CH₂), 68.4 (CH₂×4), 53.6 (CH), 49.7 (CH), 37.2 (CH₂), 31.9 (CH₂), 31.7 (CH₂).

(Compound 23b)

¹H-NMR (CDCl₃, 400 MHz) δ (ppm): 2.22-2.58 (4H, m), 2.92 (1H, dd, J=9.0, 5.0 Hz), 3.11 (1H, dd, J=9.0, 3.5 Hz), 3.29-3.80 (32H, m), 4.07-4.14 (1H, m), 4.16-4.23 (1H, m), 4.46 (16H, s), 4.64 (1H, ddd, J=6.0, 5.0, 3.5 Hz), 6.38 (1H, d, J=6.0 Hz), 7.00 (1H, d, J=6.0 Hz), 6.91-7.47 (45H, m), 8.10 (1H, d, J=6.0Hz).

¹³C-NMR (CDCl₃, 75 MHz) δ (ppm): 173.5 (C), 172.8 (C), 172.6 (C), 166.9 (C), 168.4 (C), 138.2 (C), 138.2 (C), 138.1 (C), 138.1 (C), 138.1 (C), 138.0 (C), 138.0 (C), 137.9 (C), 136.4 (C), 129.3, 128.5, 128.4, 128.4, 128.3, 127.9, 127.8, 127.8, 127.7, 127.7 and 126.9 (CH×45H), 78.9 (CH), 78.9 (CH), 78.7 (CH), 78.6 (CH), 73.4 (CH₂×2), 73.4 (CH₂×2), 73.3 (CH₂×4), 70.4 (CH₂), 70.4 (CH₂), 70.4 (CH₂), 70.3 (CH₂), 70.2 (CH₂), 70.2 (CH₂), 70.1 (CH₂), 70.0 (CH₂), 68.8 (CH₂×2), 68.4 (CH₂×2), 53.6 (CH), 53.3 (CH₂), 52.1 (CH₂), 50.0 (CH), 49.7 (CH), 37.1 (CH₂), 31.1 (CH₂), 28.4 (CH₂).

A catalytic amount of Pd(OH)₂ (Pd content; 20% by weight, 10 to 50 mg) was added to an ethanol solution (15 ml) of each of Compounds 20b to 23b (1.0 mmol) under hydrogen stream at room temperature, followed by stirring at the same temperature for 6 to 12 hours. The reaction solution was filtered through Celite 535, and then the solvent was evaporated under reduced pressure to give Compounds 25b to 28b, respectively (yield 89 to 97%).

(Compound 25b)

¹H-NMR (CD₃OD, 400 MHz) δ (ppm): 2.36-2.50 (4H, m), 2.95 (1H, dd, J=14.0, 9.0 Hz), 3.18 (1H, dd, J=14.0, 5.0 Hz), 3.30 (2H, t, J=6.0 Hz), 3.56 (2H, t, J=6.0 Hz), 4.64 (1H, dd, J=9.0, 5.0 Hz), 7.16-7.30 (5H, m).

¹³C-NMR (CD₃OD, 75 MHz) δ (ppm): 174.9 (C), 174.7 (C), 174.5 (C), 138.4 (C), 130.3 (CH×2), 129.4 (CH×2), 127.8 (CH), 61.6 (CH₂), 55.1 (CH), 43.0 (CH₂), 38.4 (CH₂), 32.2 (CH₂), 32.0 (CH₂).

(Compound 26b)

¹H-NMR (CD₃OD, 400 MHz) δ (ppm): 2.52-2.59 (4H, m), 3.00-3.21 (2H, m), 3.62-3.75 (4H, m), 4.00-4.04 (1H, m), 4.60-4.66 (1H, m), 7.35-7.49 (5H, m).

¹³C-NMR (CD₃OD, 75 MHz) δ (ppm): 174.8 (C), 174.7 (C), 174.7 (C), 138.3 (C), 130.2 (CH×2), 129.4 (CH×2), 127.7 (CH), 62.0 (CH₂×2), 55.1 (CH), 54.4 (CH), 38.4 (CH₂), 32.3 (CH₂), 32.0 (CH₂).

(Compound 27b)

¹H-NMR (CD₃OD, 400 MHz) δ (ppm): 2.53-2.63 (4H, m), 3.11 (1H, dd, J=11.0, 7.0 Hz), 3.32 (1H, dd, J=11.0, 4.0 Hz), 3.24 (1H, dd, J=11.0, 5.0 Hz), 4.66 (1H, t, J=5.0 Hz), 7.17-7.28 (5H, m).

¹³C-NMR (CD₃OD, 75 MHz) δ (ppm): 174.6 (C), 174.4 (C), 135.8 (C), 129.4 (CH), 128.6 (CH), 127.2 (CH), 53.2 (CH), 37.3 (CH₂), 29.5 (CH₂), 9.7 (CH₃).

EXAMPLE 6

Synthesis of Chemically Modified Low Molecular Compounds Modified with the Compound of the Present Invention (Other Method for Synthesizing Compounds 25a to 28a):

The reaction scheme is shown below.

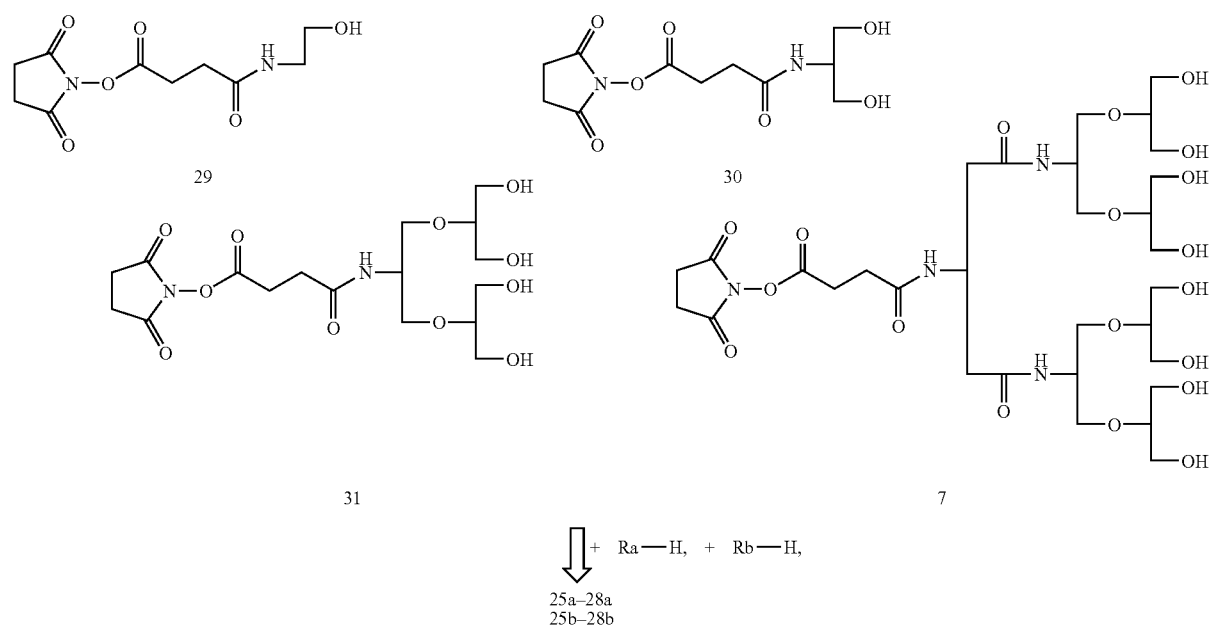

3.62-3.81 (14H, m), 4.21 (1H, q, J=4.0 Hz), 4.71-4.75 (1H, m), 7.36-7.49 (5H, m).

¹³C-NMR (CD₃OD, 75 MHz) δ (ppm): 174.5 (C), 174.3 (C), 173.3 (C), 138.1 (C), 130.1 (CH), 130.1 (CH), 129.3 (CH), 129.3 (CH), 127.7 (CH), 82.7 (CH×2), 69.4 (CH₂×2), 62.3 (CH₂×2), 62.2 (CH₂×2), 54.9 (CH), 50.8 (CH), 38.2 (CH₂), 32.0 (CH₂), 31.8 (CH₂).

(Compound 28b)

¹H-NMR (CD₃OD, 400 MHz) δ (ppm): 2.49-2.52 (4H, m), 2.93 (1H, dd, J=11.0, 6.0 Hz), 3.19 (1H, dd, J=11.0, 4.0 Hz), 3.30-3.79 (28H, m), 4.00-4.03 (2H, m), 4.13-4.18 (2H, m), 4.18-4.23 (2H, m), 4.45-4.51 (1H, m), 7.19-7.29 (5H, m).

¹³C-NMR (D₂O:CD₃OD=20:1, 75 MHz) δ (ppm): 176.4 (C), 175.1 (C), 172.2 (C), 172.1 (C), 171.7 (C), 137.8 (C), 130.2 (CH×2), 129.6 (CH×2), 127.9 (CH), 82.0 (CH×4), 69.3 (CH₂×4), 61.6 (CH₂×4), 61.5 (CH₂×4), 55.5 (CH), 53.9 (CH₂), 53.4 (CH₂), 51.0 (CH), 50.7 (CH), 37.9 (CH₂), 31.1 (CH₂), 28.7 (CH₂).

Compound 24b [(3-phenyl-(S)-2-propionyl)aminopropionic acid] was obtained in the same manner as in the above by using L-phenylalanine methyl ester hydrochloride (Rb-H.HCl) and NHS ester of propionic acid.

¹H-NMR (CD₃OD, 400 MHz) δ (ppm): 1.02 (3H, t, J=6.0 Hz), 2.16 (2H, q, J=6.0 Hz), 3.13 (1H, dd, J=11.0, 5.0 Hz), A catalytic amount of Pd(OH)₂/C (Pd content: 20% by weight, 10 to 50 mg) was added to an ethanol solution (15 ml) of each of Compounds 17 to 19 (1.0 mmol) under hydrogen stream at room temperature, followed by stirring at the same temperature for 6 to 12 hours. The reaction solution was filtered through Celite 535, and then the solvent was evaporated under reduced pressure to give Compounds 29 to 31, respectively (yield 62 to 100%).

(Compound 29)

¹H-NMR (CD₃OD, 400 MHz) δ (ppm): 2.71 (2H, t, J=5.0 Hz), 2.97 (4H, s), 3.22 (2H, t, J=5.0 Hz), 3.49 (2H, t, J=5.0 Hz), 3.59 (2H, t, J=5.0 Hz).

(Compound 30)

¹H-NMR (CD₃OD, 400 MHz) δ (ppm): 2.72 (2H, t, J=5.0 Hz), 2.89 (4H, s), 3.01 (2H, t, J=5.0 Hz), 3.66 (4H, d, J=4.5 Hz), 3.90-3.98 (1H, m).

(Compound 31)

¹H-NMR (CD₃OD, 400 MHz) δ (ppm): 2.69 (2H,, t, J=5.0 Hz), 2.89 (4H, s), 3.01 (2H, t, J=5.0 Hz), 3.60-3.82 (14H, m), 4.14-4.21 (1H, m).

¹³C-NMR (CD₃O, 300 MHz) δ (ppm): 172.8 (C), 171.5 (C×2), 169.6 (C), 83.0 (CH×2), 69.6 (CH₂×2), 62.5 (CH₂×2), 62.3 (CH₂×2), 51.2 (CH), 31.0 (CH₂), 27.5 (CH₂), 26.5 (CH₂×2).

Compound Ra-H (1.0 mmol, 285 mg) and each of Compounds 29 to 31 and 7 (2.0 mmol) were stirred in 5% aqueous dipotassium hydrogenphosphate solution (5 ml) at room temperature for 1 hour to give Compounds 25a to 28a, respectively (when compared with the samples synthesized in Example 4, it was confirmed that they are respectively the same compounds).

EXAMPLE 7

Synthesis of Chemically Modified Low Molecular Compounds Modified with the Compound of the Present Invention [Other Method for Synthesizing Compounds 25b to 28b]:

L-phenylalanine (Rb-H, 1.0 mmol, 165 mg) and each of Compounds 29 to 31 and 7 (2.0 mmol) were stirred in 5% aqueous dipotassium hydrogenphosphate solution (5 ml) at room temperature for 1 hour to give Compounds 25b to 28b, respectively (when compared with the samples synthesized in Example 5, it was confirmed that they are respectively the same compounds).

EXAMPLE 8

Synthesis of Compounds [Compounds Represented by Formula (4)]:

The reaction scheme is shown below.

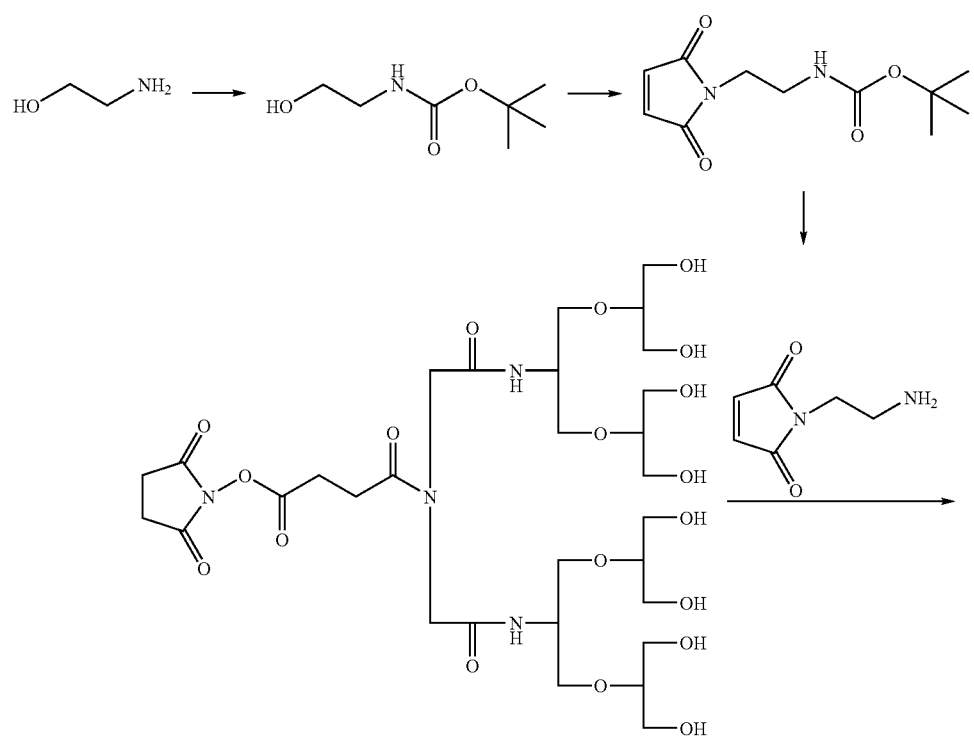

7

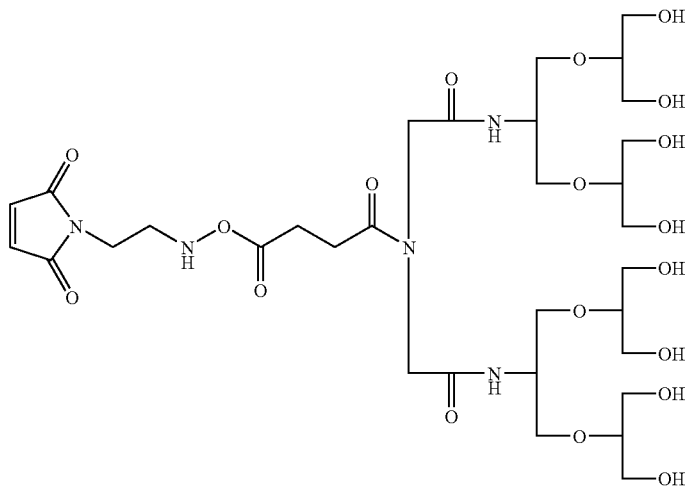

33

Ethanolamine (500 mg, 8.2 mmol) and sodium hydroxide (1.7 g, 40 mmol) were suspended in a rinsed solvent of dioxane and water (10:1, 50 ml), and di-tert-butyl dicarbonate (1.96 g, 9.0 mmol) was added to the thus obtained suspension in several portions at 0° C. The reaction solution was stirred at 0° C. for 2 hours, and then an aqueous potassium hydrogensulfate solution (5%, 50 ml) was added thereto, followed by extraction with ethyl acetate (150 ml). The extracted organic layer was washed with water (30 ml) and a saturated brine (30 ml) in this order, dried over anhydrous magnesium sulfate and then filtered. The solvent was evaporated under reduced pressure to give crude (2-hydroxyethyl)carbamic acid terbutyl ester (1.32 g, 8.2 mmol, yield 100%).

A toluene solution of Mitsunobu reagent (diethyl azodicarboxylate) (1.106 g/ml, 8.2 mmol, 1.29 ml) was gradually added to a tetrahydrofuran solution (25 ml) of triphenylphosphine (2.15 g, 8.2 mmol) at −78° C. To the thus obtained solution, a tetrahydrofuran solution (5 ml) of (2-hydroxyethyl)carbamic acid tert-butyl ester (1.32 g, 8.2 mmol) and maleimide (794 mg, 8.2 mmol) was added, followed by stirring at −78° C. for 5 minutes and further stirring at room temperature for 36 hours. The thus obtained reaction solution was concentrated, ether was added thereto, and the formed precipitate was removed by filtration. The thus obtained filtrate was concentrated, and the resulting residue was purified by silica gel column chromatography (hexane:ethyl acetate=1:1) to give 2-(maleimido)ethylcarbamic acid tert-butyl ester (531 mg, 2.53 mmol, yield 31%).

$^1$H-NMR (CDCl$_3$, 400 MHz) δ (ppm): 6.72 (2H, s), 4.75 (1H, br, NH), 3.66 (2H, t, J=5.6 Hz), 3.33 (2H, dt, J=5.1, 5.6 Hz), 1.40 (9H, s).

(2-Maleimido)ethylcarbamic acid tert-butyl ester (48 mg, 0.2 mmol) was dissolved in a mixed solvent of trifluoroacetic acid and dichloromethane (30:70, 5 ml), followed by stirring at 0° C. for 2 hours, and then the reaction solution was concentrated. The thus obtained residue was dissolved in dichloromethane (20 ml), and a saturated aqueous sodium hydrogencarbonate solution (10 ml) was added thereto to separate the layers. The organic layer was dried over potassium hydrogencarbonate and filtered. The solvent was evaporated under reduced pressure to give 1-(2-aminoethyl)-3-pyrroline-2,5-dione (28 mg, 0.2 mmol, yield 100%).

Compound 7 (77.2 mg, 0.1 mmol) and 1-(2-aminoethyl)-3-pyrroline-2,5-dione (28.0 mg, 0.2 mmol) were suspended in water (5 ml), followed by stirring at room temperature for 2 hours. The reaction solution was concentrated, and the thus obtained residue was purified by preparative reverse phase tin layer chromatography (preparative reverse phase TLC) (water:methanol=10:1) to give Compound 33 (39 mg, 0.05 mmol, yield 50%).

$^1$H-NMR (CD$_3$OD, 300 MHz) δ (ppm): 6.56 (2H, s), 4.22-4.05 (6H, m), 3.80-3.43 (32H, m), 2.96-2.74 (4H, m).

EXAMPLE 9

Synthesis of Compounds [Compounds Represented by Formula (5)]:

The reaction scheme is shown below. In the reaction formula, Bn represents benzyl.

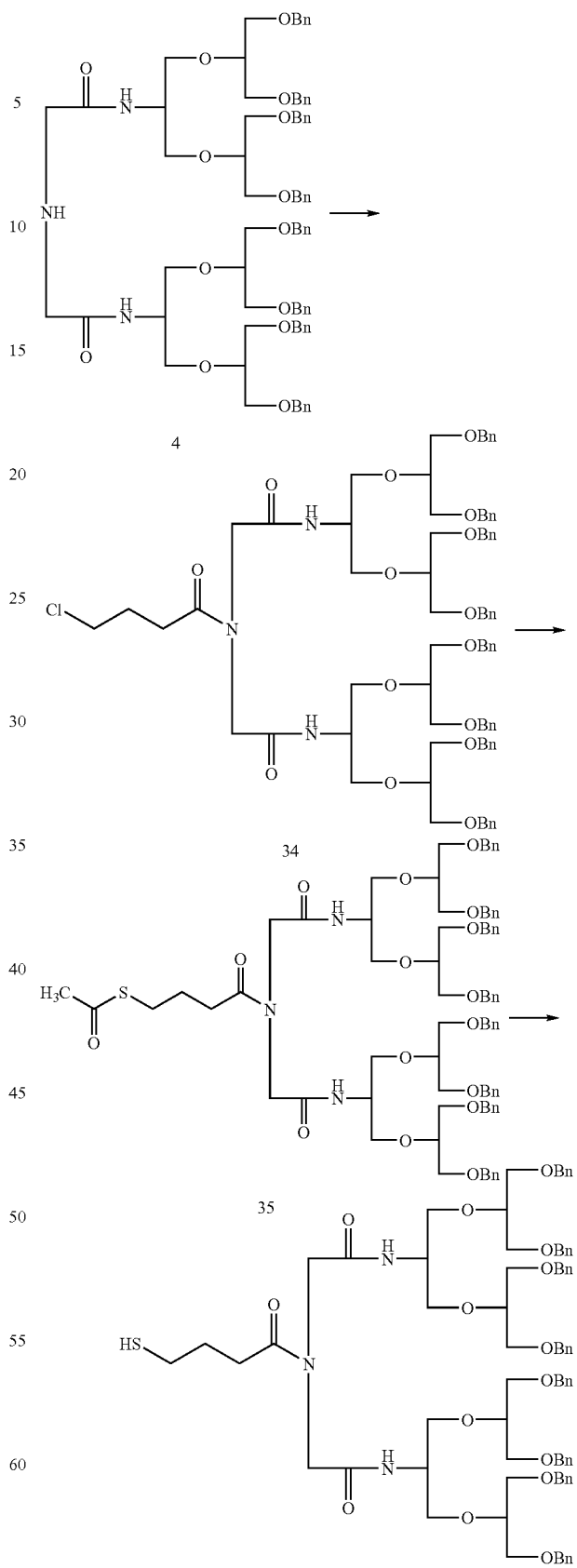

Compound 34 was prepared in accordance with the method described in *J. Org. Chem.,* 50. 1148-1156 (1990). A tetrahydrofuran solution (3 ml) of Compound 4 (300 mg, 0.231 mmol) was cooled to 0° C., and 60% sodium hydride (10.2 mg, 0.255 mmol) was added thereto, followed by stirring for 10 minutes. To the reaction solution, 4-chlorobutyric acid chloride (0.028 ml, 0.255 mmol) was added, followed by stirring for 10 minutes and further stirring at room temperature for 8 hours. To the reaction solution, 1 mol/l hydrochloric acid was added thereto, followed by extraction with ethyl acetate. The organic layer was washed with a saturated brine, dried over anhydrous magnesium sulfate and then filtered. The solvent was evaporated under reduced pressure, and the residue was purified by silica gel column chromatography (hexane:ethyl acetate 1:2) to give Compound 34 (231.6 mg, 0.165 mmol, yield 71%).

$^1$H-NMR (CDCl$_3$, 400 MHz) δ (ppm): 8.38 (1H, d, J=8 Hz, CONH, 7.33-7.21 (40H, m), 6.99 (1H, d, J=7.2 Hz, CONH) 4.46 (16H, s), 4.25-4.06 (2H, m), 3.80-3.37 (34H, m), 2.29 (2H, t, J=6.8 Hz), 1.97 (2H, quint, J=6.4 Hz).

$^{13}$C-NMR (CDCl$_3$, 100 MHz) δ (ppm): 172.4 (C), 168.5 (C), 167.9 (C), 138.0 (C×2), 138.0 (C×2), 137.9 (C×2), 137.9 (C×2), 128.1, 128.1, 128.1, 127.6, 127.4, 127.3 and 127.3 (CH×40), 78.9 (CH×2), 78.5 (CH×2), 73.3 (CH$_2$×2), 73.2 (CH$_2$×2), 73.1 (CH$_2$×4), 70.4 (CH$_2$×2), 70.1 (CH$_2$×2), 69.9 (CH$_2$×2), 69.8 (CH$_2$×2), 68.8 (CH$_2$×2), 68.2 (CH$_2$×2), 53.5 (CH$_2$), 52.2 (CH$_2$), 49.8 (CH), 49.5 (CH), 44.4 (CH$_2$), 29.2 (CH$_2$), 27.4 (CH$_2$).

Compound 35 was prepared in accordance with the method described in *J. Am. Chem. Soc.,* 111. 285 -291 (1989).

Thioacetic acid (0.024 ml, 0.331 mmol) and sodium ethoxide (22.5 mg, 0.331 mmol) were added at room temperature to ethanol solution (50 ml) of Compound 34 (231.6 mg, 0.165 mmol) and then refluxed for 15 hours. The reaction solution was cooled to room temperature, and 1 mol/l hydrochloric acid was added thereto, followed by extraction with ethyl acetate. The organic layer was washed with 5% aqueous sodium hydrogencarbonate solution and a saturated brine in this order, dried over anhydrous magnesium sulfate and then filtered. The solvent was evaporated under reduced pressure, and the residue was purified by silica gel column chromatography (ethyl acetate) to give Compound 35 (174.9 mg, 0.121 mmol, yield 73%).

$^1$H-NMR (CDCl$_3$, 400 MHz) δ (ppm); 8.48 (1H, d, J=7.6 Hz, CONH), 7.33-7.20 (40H, m), 6.96 (1H, d, J=8.8 Hz), 4.46 (16H, s), 4.26-4.05 (2H, m), 3.80-3.35 (32H, m), 2.80 (2H, t, J=7.2 Hz), 2.26 (3H, s), 2.19 (2H, t, J=7.0 Hz), 1.80 (2H, quint, J=7.0 Hz).

Compound 36 was prepared in accordance with the method described in *J. Am. Chem. Soc.,* 85, 1337- 1341 (1963).

To an ethanol solution (10 ml) of Compound 35 (174.9 mg, 0.121 mmol), 0.6 mol/l sodium hydroxide ethanol solution (5 ml, 3 mmol) was added at 0° C., followed by stirring at room temperature for 24 hours. To the reaction solution, 1 mol/l hydrochloric acid was added, followed by extraction with ethyl acetate. The organic layer was washed with a saturated brine, dried over anhydrous magnesium sulfate and then filtered. The solvent was evaporated under reduced pressure, and the residue was purified by silica gel column chromatography (ethyl acetate) to give Compound 36 (113.3 mg, 0.079 mmol, yield 67%).

$^1$H-NMR (CDCl$_3$, 400 MHz) δ (ppm) 8.53 (1H, d, J=8.0 Hz), 7.35-7.18 (40H, m), 6.98 (1H, d, J=8.4 Hz), 4.45 (16H, s), 4.27-4.05 (2H, m), 3.81-3.32 (32H, m), 2.55 (2H, t, J=6.8 Hz), 2.23 (2H, t, J=7.0 Hz), 1.90 (2H, quint, J=6.8 Hz)

$^{13}$C-NMR (CDCl$_3$, 100 MHz) δ (ppm): 172.7 (C), 168.6 (C), 168.1 (C), 138.1 (C×2), 138.0 (C×2), 137.9 (C×2), 137.9 (C×2), 128.1, 128.1, 127.6, 127.4, 127.3 and 127.3 (CH×40), 78.8 (CH×2), 78.5 (CH×2), 73.3 (CH$_2$×2), 73.1 (CH$_2$×2), 73.1 (CH$_2$×4), 70.3 (CH$_2$×2), 70.1 (CH$_2$×2), 69.9 (CH$_2$×2), 69.8 (CH$_2$×2), 68.8 (CH$_2$×2), 68.2 (CH$_2$×2), 53.6 (CH$_2$), 52.2 (CH$_2$), 49.8 (CH), 49.4 (CH), 37.3 (CH$_2$), 30.5 (CH$_2$), 23.7 (CH$_2$).

EXAMPLE 10

Preparation of Chemically Modified Sterols Modified With the Compound of the Present Invention:

The reaction scheme is shown below. In the reaction scheme, Bn represents benzyl group.

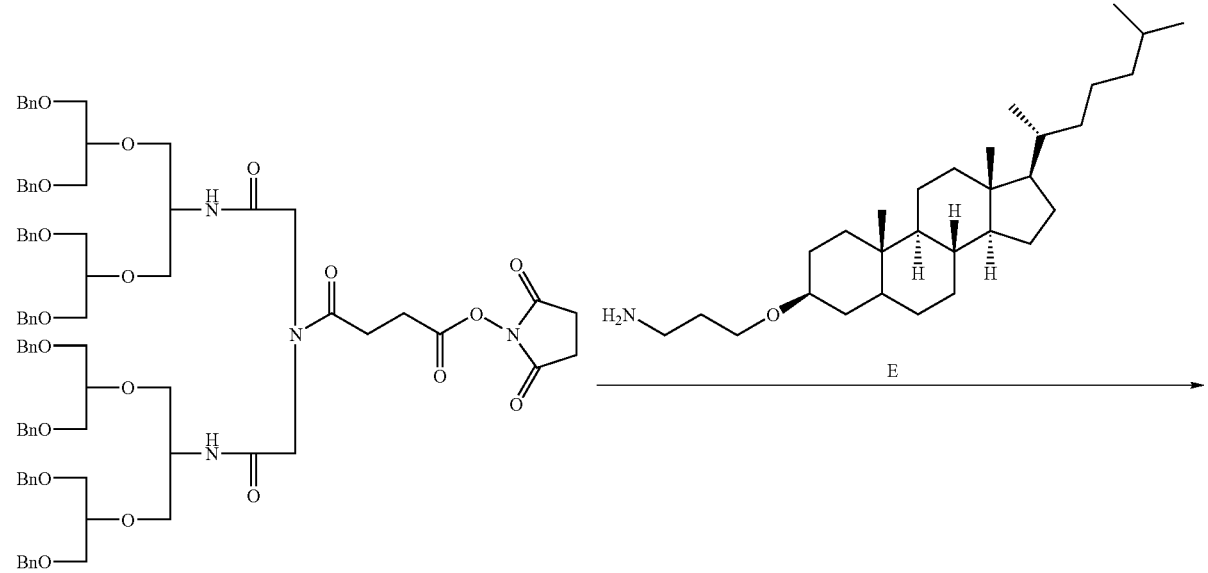

-continued

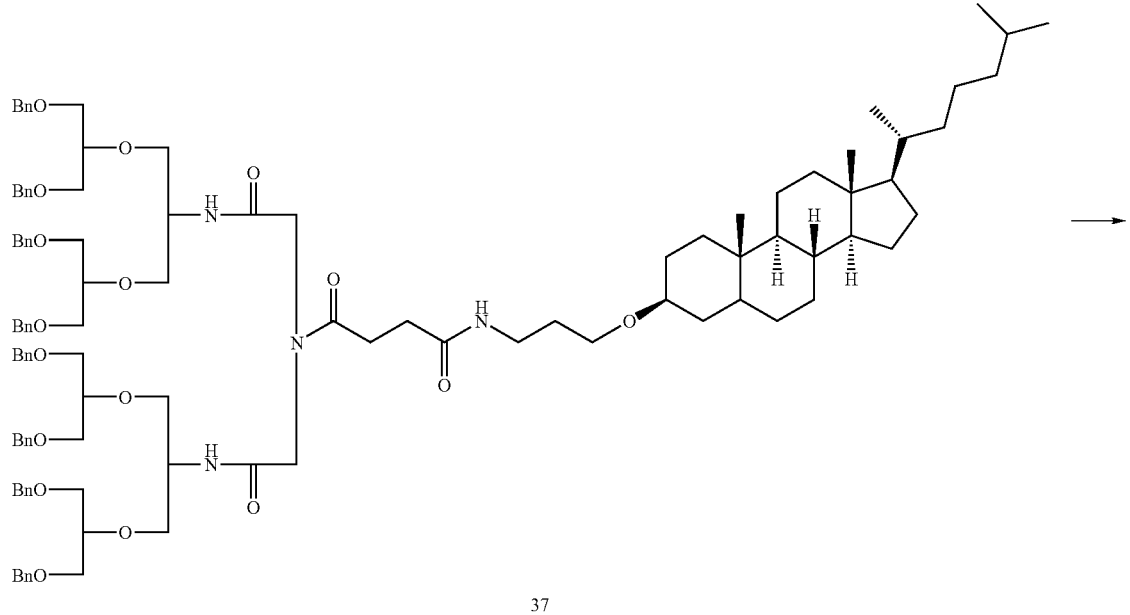

37

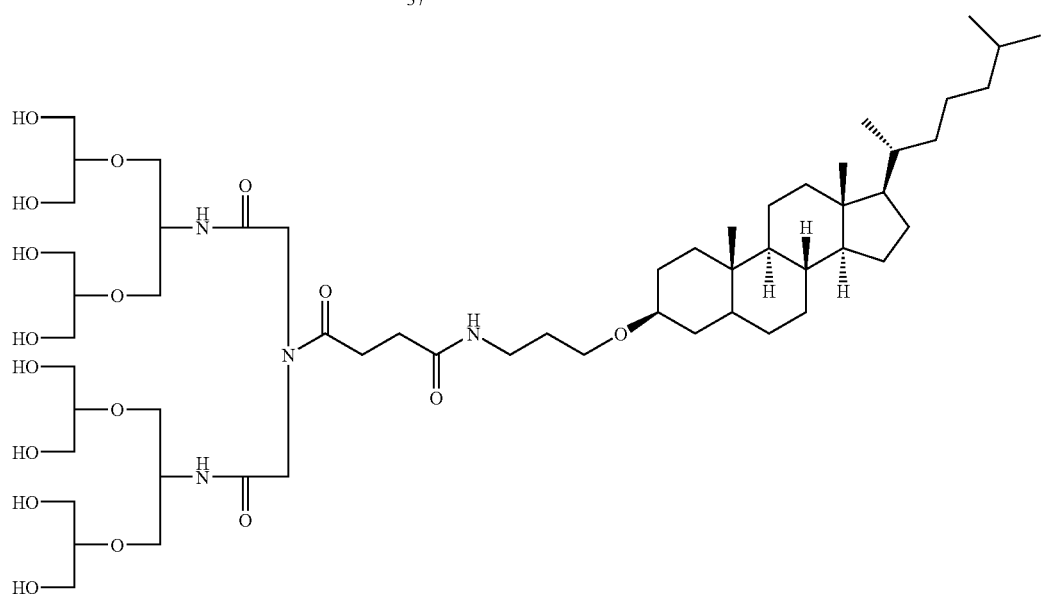

38

Compound E (1.43 g, 3.22 mmol) and dimethylaminopyridine (DMAP; 0.79 g, 6.44 mmol) were added to a tetrahydrofuran solution of Compound 6 (2.4 g, 1.61 mmol) in this order at room temperature, followed by stirring at the same temperature for 2 hours. The reaction solution was poured into 5% aqueous potassium hydrogen sulfate solution, followed by extraction with ethyl acetate. The organic layer was washed with a saturated aqueous sodium hydrogencarbonate solution and a saturated brine in this order, dried over anhydrous magnesium sulfate and then filtered. The solvent was evaporated under reduced pressure, and the residue was purified by silica gel column chromatography (chloroform:methanol=20:1) to give Compound 37 (2.45 g, 1.33 mmol, yield 83%).

$^1$H-NMR (CDCl$_3$, 400 MHz) δ (ppm): 8.28-8.22 (1H, m, CONH), 8.35-8.19 (m, 40H), 7.10-7.00 (1H, m, CONH), 6.17-6.09 (1H, m, CONH), 4.51-4.43 (16H, m), 3.80-3.40 (36H, m), 3.26-3.20 (2H, m), 3.19-3.08 (1H, m), 2.48-2.41 (2H, m), 2.35-2.29 (2H, m), 2.00-0.80 (33H, m), 0.90 (3H, d, J=6.4 Hz), 0.86 (6H, d, J=6.4 Hz), 0.77 (3H, s), 0.63 (3H, s).

13C-NMR (CDCl$_3$, 75MHz) δ (ppm): 173.1 (C), 171.5 (C), 168.1 (C), 138.2 (C), 128.3, 127.6 and 127.5 (CH×40), 78.9 (CH×4) 70.4 (CH$_2$×8), 70.0 (CH$_2$×8), 68.4 (CH$_2$×4), 66.4 (CH$_2$), 56.5 (CH), 56.3 (CH), 54.4 (CH), 52.3 (CH$_2$×2), 44.8 (CH×2), 42.6 (C), 40.0 (CH$_2$), 39.5 (CH$_2$), 38.0 (CH$_2$), 37.0 (CH$_2$), 36.2 (CH$_2$), 35.8 (CH), 35.8 (C), 35.5 (CH), 34.8 (CH$_2$), 32.1 (CH$_2$), 31.1 (CH$_2$), 31.0 (CH$_2$), 29.6 (CH$_2$), 28.9 (CH$_2$), 28.3 (CH$_2$), 28.3 (CH$_2$), 28.0 (CH), 24.3 (CH$_2$), 23.9 (CH$_2$), 22.9 (CH$_3$), 22.6 (CH$_3$), 21.3 (CH$_2$), 18.7 (CH$_3$), 12.4 (CH), 12.1 (CH$_3$)

To an ethanol solution (15 ml) of Compound 37 (2.45 g, 1.33 mmol), Pd(OH)$_2$/C (Pd content: 20% by weight, 260 mg) was added under hydrogen stream at room temperature, followed by stirring at the same temperature for 3 hours. The reaction solution was filtered through Celite 535, and then the solvent was evaporated under reduced pressure to give Compound 38 (1.52 g, 1.33 mmol, yield 100%).

$^1$H-NMR (CD$_3$OD, 400 MHz) δ (ppm): 4.33-4.12 (4H, m), 4.08-3.99 (2H, m), 3.93-3.36 (32H, m), 3.27-3.17 (1H, m), 2.66-2.43 (4H, m), 2.07-0.85 (33H, m), 0.93 (3H, d, J=6.8 Hz), 0.88 (6H, d, J=6.8 Hz), 0.82 (3H, s), 0.69 (3H, s).

REFERENCE EXAMPLE 1

Preparation of G-CSF derivative:

A human G-CSF (hG-CSF) derivative having the amino acid sequence represented by SEQ ID NO:1 or SEQ ID NO:2, in which threonine at 1st position of hG-CSF was replaced with alanine, leucine at 3rd position was replaced with threonine, glycine at 4th position was replaced with tyrosine, proline at 5th position was replaced with arginine and cysteine at 17th position was replaced with serine, was prepared by the method described in Japanese Published Examined Patent Application No. 096558/95. Also, the SEQ ID NO:1 contains Met in the N-terminus as a signal peptide amino acid.

*Escherichia coli* W3110strA (*Escherichia coli* ECfBD28 FERM BP-1479) having a plasmid pCfBD28 comprising a DNA encoding the above-described hG-CSF derivative was cultured at 37° C. for 18 hours in an LG medium (prepared by dissolving 10 g of Bacto-trypton, 5 g of yeast extract, 5 g of sodium chloride and 1 g of glucose in 1 liter of water, and adjusting its pH to 7.0 with NaOH), 5 ml of this culture was inoculated into 100 ml of an MCG medium (Na$_2$HPO$_4$ 0.6%, KH$_2$PO$_4$ 0.3%, sodium chloride 0.5%, casamino acid 0.5%, MgSO$_4$ 1 mmol/l, vitamin B, 4 μg/ml, pH 7.2) containing 25 μg/ml of tryptophan and 50 μg/ml of ampicillin and cultured at 30° C. for 4 to 8 hours, and then 10 μg/ml of 3β-indole-acrylic acid as tryptophan inducing substance was added thereto, followed by further culturing for 2 to 12 hours. The cells were collected by centrifuging the culture at 8,000 rpm for 10 minutes and washed with 30 mmol/l sodium chloride and 30 mmol/l Tris-HCl buffer (pH 7.5).

The washed cells were suspended in 30 ml of the above-described buffer solution and subjected to ultrasonic disintegration at 0° C. for 10 minutes (SONIFIER CELL DISRUPTOR200 manufactured by BRANSON SONIC POWER COMPANY, OUTPUT CONTROL 2). The ultrasonic disintegration product was centrifuged at 9,000 rpm for 30 minutes to obtain a cell residue.

The hG-CSF derivative was extracted, purified, solubilized and regenerated from the cell residue in accordance with the method of Marston et al. [*Bio/Technology*, 2, 800 (1984)].

REFERENCE EXAMPLE 2

Preparation of Polyethylene Glycol-Modified G-CSF Derivative:

To 995 ml of the G-CSF derivative of Reference Example 1 which had been prepared into 4.0 mg/ml with 50 mmol/l phosphate buffer (pH 7.6), 19.1 g (4.5 mol per 1 mol protein) of an activated PEG derivative (M-SPA-20,000 manufactured by Shearwater Polymers, Inc., about 20,000 in average molecular weight) was added and the reaction was carried out at 4° C. for a day and night. Next, the reaction product was purified by passing through 2,000 ml of SP Sepharose FF column (manufactured by Amersham-Pharmacia Biotech) which had been equilibrated with 20 mmol/l acetate buffer (pH 4.5).

Then, 4,000 ml of the desired fractions were centrifuged to obtain 320 ml of a solution containing 11.2 mg/ml of the desired product (yield 90.4%).

<Electrophoresis>

SDS-PAGE was carried out by using 4 to 20% gradient gel (PAGEL SPG-520L, manufactured by ATTO) in the absence of 2-mercaptoethanol to confirm bands of 1 to 3 molecules-bound substance.

<Gel Filtration HPLC Analysis>

Using 2 columns of TSK gel G4000SW$_{XL}$ (7.8×300 mm×2 columns connected, manufactured by Tosoh), the analysis was carried out by the following method.

| | |
|---|---|
| Retention time: | 38.2 minutes (1 molecule-bound substance) |
| | 34.4 minutes (2 molecules-bound substance) |
| | 32.2 minutes (3 molecules-bound substance) |
| Mobile phase: | 150 mmol/l sodium chloride, 20 mmol/l sodium acetate buffer (pH 4.5) |
| Flow rate: | 0.5 ml/min |
| Detection: | UV 280 nm |

REFERENCE EXAMPLE 3

Synthesis of 3-(3β,5α-cholestanoxy)propyl-1-amine (Compound E)

The reaction scheme is shown below. In the reaction scheme, Ts represents tosyl.

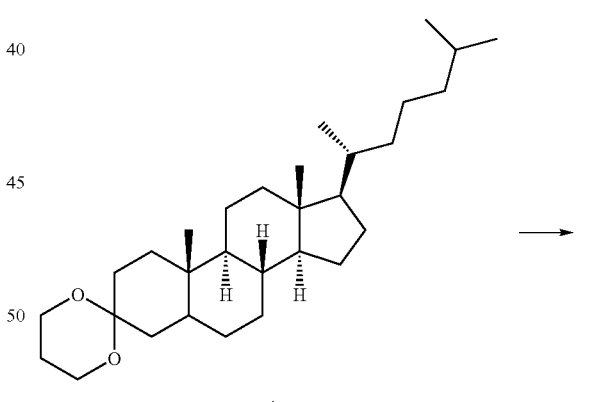

A

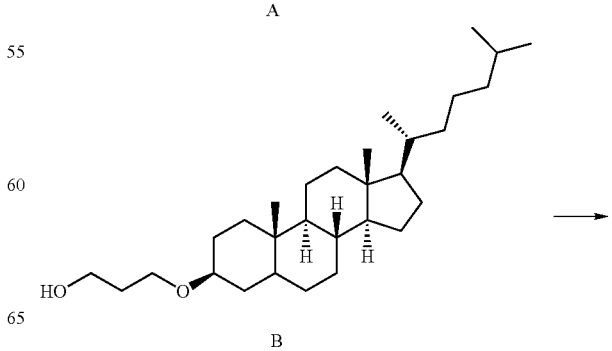

B

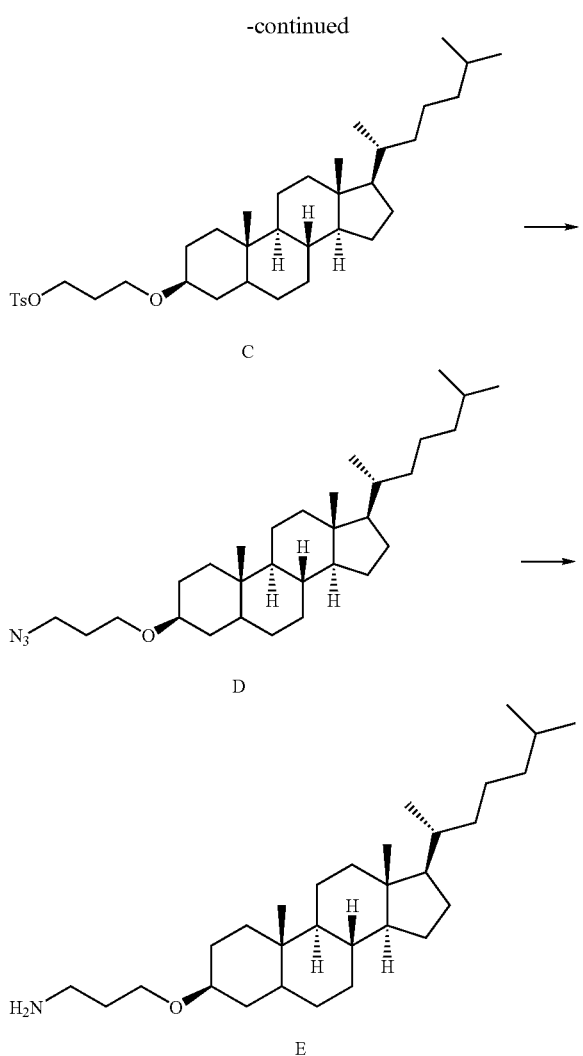

Compound A was synthesized by the method described in *J. Chem. Soc., Perkin Trans.* 1, 1, 158-160 (1979).

Compound B was synthesized by the method described in *J. Org. Chem.*, 58 6756-6765 (1993). A dichloromethane solution (4 ml) of Compound A (556 mg, 1.25 mmol) was cooled to −78° C., and $BH_3 \cdot S(CH_3)_2$ (0.47 ml, 5 mmol) and trimethylsilyl triturate (TMSOTf; 0.9 ml, 5 mmol) was added thereto, followed by stirring at the same temperature for 15 minutes. The reaction solution was poured into an aqueous sodium hydrogencarbonate solution, followed by extraction with dichloromethane. The organic layer was dried over anhydrous magnesium sulfate and then filtered. The solvent was evaporated under reduced pressure, and the residue was purified by silica gel column chromatography (hexane:ethyl acetate=3:1) to give Compound B [3-(3β,5α-cholestanoxy)propan-1-ol; 279 mg, 0.63 mmol, yield 50%].

$^1$H-NMR (CDCl$_3$, 400 MHz) δ (ppm): 3.78 (2H, t, J=6.4 Hz), 3.67 (2H, t, J=6.4 Hz), 3.23 (1H, dddd, J=6.4, 6.4, 14.4, 14.4 Hz), 2.67 (1H, brs, OH), 2.00-0.81 (33H, m), 0.90 (3H, d, J=6.4 Hz), 0.86 (6H, d, J=6.8 Hz), 0.79 (3H, s), 0.64 (3H, s).

$^{13}$C-NMR (CDCl$_3$, 75 MHz) δ (ppm): 79.7 (CH), 68.3 (CH$_2$), 63.3 (CH$_2$), 57.1 (CH), 56.9 (CH), 55.0 (CH), 45.5 (CH), 43.2 (C), 40.7 (CH$_2$), 40.2 (CH$_2$), 37.6 (CH$_2$), 36.8 (CH$_2$), 36.4 (CH), 36.4 (C), 36.1 (CH), 35.4 (CH$_2$), 32.8 (CH$_2$), 32.8 (CH$_2$), 29.5 (CH$_2$), 28.9 (CH$_2$), 28.9 (CH$_2$), 28.7 (CH), 24.9 (CH$_2$), 24.5 (CH2), 23.5 (CH$_3$), 23.2 (CH$_3$), 21.9 (CH$_2$), 19.3 (CH$_3$), 13.0 (CH$_3$), 12.7 (CH$_3$).

Toluenesulfonyl chloride (4.42 g, 23.16 mmol) and triethylamine (7.8 ml, 46.32 mmol) were added to a dichloromethane solution (50 ml) of Compound B (5.17 g, 11.58 mmol) was added at room temperature, followed by stirring at the same temperature for 24 hours. The reaction solution was poured into 5% aqueous potassium hydrogen sulfate solution, followed by extraction with dichloromethane. The organic layer was washed with a saturated aqueous sodium hydrogencarbonate solution and a saturated brine in this order, dried over anhydrous magnesium sulfate and then filtered. The solvent was evaporated under reduced pressure to give Compound C [3-(3β,5α-cholestanoxy)propyl-4-methylbenzenesulfonate 6.95 g, 11.58 mmol, yield 100%].

Sodium azide (2.86 g, 44 mmol) was added to a DMF solution (40 ml) of Compound C (6.95 g, 11.58 mmol) at room temperature, followed by stirring at 120° C. for 3 hours. The reaction solution was cooled to room temperature, and poured into a saturated aqueous sodium hydrogencarbonate solution, followed by extraction with diethyl ether. The organic layer was washed with a saturated brine, dried over a magnesium sulfate and then filtered. The solvent was evaporated under reduced pressure, and the residue was purified by silica gel column chromatography (hexane:ethyl acetate=3:1) to give Compound D [3-(3β,5α-cholestanoxy)propyl-1-azide; 4.67 g, 9.91 mmol, yield 86%].

$^1$H-NMR (CDCl$_3$, 400 MHz) δ (ppm): 3.52-3.43 (2H, m), 3.36-3.29 (2H, t, J=6.8 Hz), 3.14 (1H, dddd, J=4.4, 4.4, 10.8, 10.8 Hz), 2.00-0.75 (33H, m), 0.90 (3H, d, J=6.0 Hz), 0.86 (6H, d, J=6.8 Hz), 0.72 (3H, s), 0.58 (3H, s).

$^{13}$C-NMR (CDCl$_3$, 75 MHz) δ (ppm): 78.8 (CH), 64.4 (CH$_2$), 56.5 (CH), 56.3 (CH), 54.4 (CH), 48.6 (CH$_2$), 44.8 (CH), 42.6 (C), 40.0 (CH$_2$), 39.5 (CH$_2$), 37.0 (CH$_2$), 36.2 (CH$_2$), 35.8 (CH), 35.8 (C), 35.5 (CH), 34.8 (CH$_2$), 32.1 (CH$_2$), 29.6 (CH$_2$), 28.8 (CH$_2$), 28.2 (CH$_2$), 28.2 (CH$_2$), 28.0 (CH), 24.2 (CH$_2$), 23.8 (CH$_2$), 22.8 (CH$_3$), 22.6 (CH$_3$), 21.2 (CH$_3$), 18.7 (CH$_3$), 12.3 (CH$_3$), 12.1 (CH$_3$).

To an ethanol solution (25 ml) of Compound D (1.97 g, 4.18 mmol), Pd(OH)$_2$/C (Pd content: 20% by weight, 230 mg) was added under hydrogen stream at room temperature, followed by stirring at the same temperature for 12 hours. The reaction solution was filtered through Celite 535, and then the solvent was evaporated under reduced pressure to give Compound E [3-(3β,5α-cholestanoxy)propyl-1-amine; 1.86 g, 4.18 mmol, yield 100%].

$^1$H-NMR (CDCl$_3$, 400 MHz) δ (ppm): 3.60-3.49 (2H, m), 3.20 (1H, dddd, J=4.4, 4.4, 10.4, 10.4 Hz), 2.81 (2H, t, J=6.4 Hz), 2.07-0.81 (33H, m), 0.90 (3H, d, J=6.0 Hz), 0.86 (6H, d, J=5.6 Hz), 0.79 (3H, s), 0.64 (3H, s).

INDUSTRIAL APPLICABILITY

The compound disclosed in the present invention is useful in chemically modifying a physiologically active polypeptide or a derivative thereof or a low molecular compound. Also, chemically modified polypeptides and the like modified with the compound can be produced under such conditions that not only their stability or water-solubility is improved but also their physiological activity is markedly maintained in comparison with the conventional chemically modified polypeptides and the like. Since the chemically modified polypeptides and the like of the present invention show their physiological activities effectively for a prolonged period of time when administered into the living body, they are useful as improving agents or therapeutic agents for the symptoms related to the physiological activities. In addition, since chemically modified low molecular compounds modified with the compound show improved stability or water-solubility, they are useful as low molecular pharmaceutical preparations, solubilizer for low molecular reagent or the like.

Free Text of Sequence Listing:

SEQ ID NO:1—Explanation of artificial sequence: 5 amino acids-substituted peptide of hG-CSF SEQ ID NO:2—Explanation of artificial sequence: 5 amino acids-substituted peptide of hG-CSF

The invention claimed is:

1. A compound represented by formula (1):

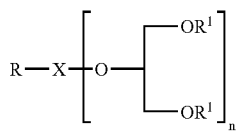

(1)

wherein R is selected from
(i) the group consisting of a caboxylic acid active ester, carbonate, maleimido, mercapto, formyl, tresyl, isocyanato, an acid anhydride, an acid halide, vinylsulfonyl, hydrazido, amino, a hydroxyl group, halogen, carboxy, vinyl and phosphono, and
(ii) the group consisting of a carboxylic acid active ester, carbonate, maleimido, mercapto, formyl, tresyl, isocyanato, an acid anhydride, an acid halide, vinylsulfonyl, hydrazido, amino, a hydroxyl group, halogen, carboxy, vinyl and phosphono, which are bound to a moiety which is at least one member selected from the group consisting of substituted or unsubstituted alkylene, carbonyl, substituted or unsubstituted imino, O and S;

n represents an integer of 3 to 1024; and

X represents a structure in which this branching is repeated.

2. The compound according to claim 1, wherein

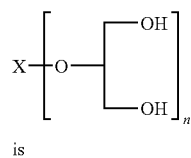

is

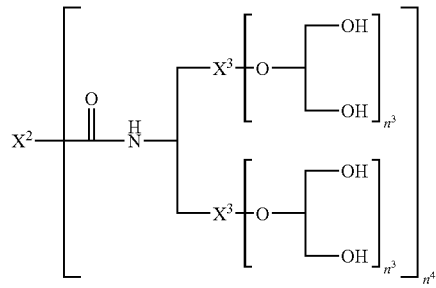

wherein $n^3$ and $n^4$ each represents an integer;

$X^2$ represents a single bond or

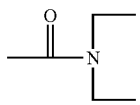

or a structure in which this branching is repeated;

$X^3$ represents a single bond or

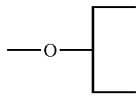

or a structure in which this branching is repeated.

3. The compound according to claim 1, wherein n is $2^m$, in which m is an integer of 2 to 16.

4. The compound according to claim 1, wherein n is 4, 8, 16 or 32.

5. The compound according to claim 1, wherein X represents a structure in which the following branching is repeated 2 or more times,

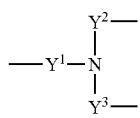

wherein A represents CH or N,

Y$^1$, Y$^2$ and Y$^3$ each independently represent a single bond, or one, or two or more in any combination, which may be the same or different, selected from the group consisting of substituted or unsubstituted alkylene, carbonyl, substituted or unsubstituted imino, O, S, sulfonyl and sulfinyl, and when A, Y$^1$, Y$^2$ and Y$^3$ exist two or more in number, they may be the same or different.

6. A mixture comprising at least two compounds described in claim 1.

7. The compound according to claim 2, wherein R is N-hydroxysuccinimide ester-unsubstituted ethylene, n$^3$ is 1, n$^4$ is 2, X$^2$ is

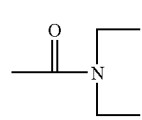

and X$^3$ is a single bond, providing formula (2):

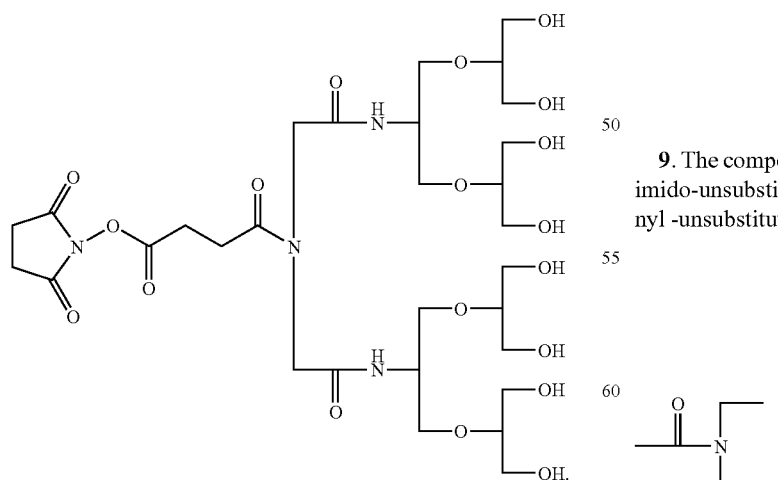

(2)

8. The compound according to claim 2, wherein R is N-hydroxysuccinimide ester-unsubstituted ethylene, n$^3$ is 1, n$^4$ is 4, X$^2$ is

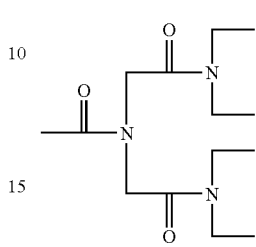

and X$^3$ is a single bond, providing formula (3):

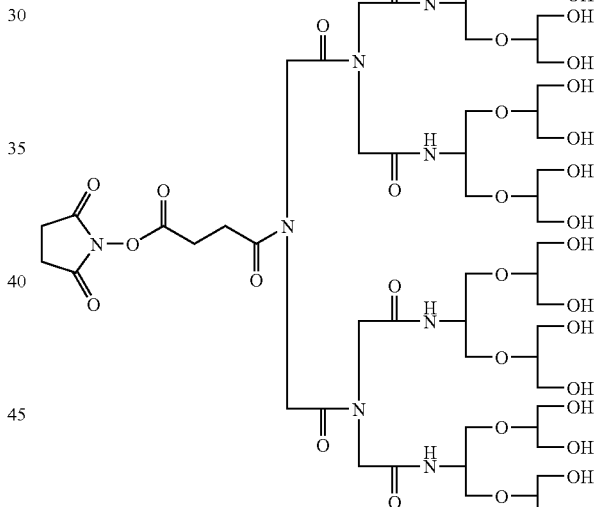

(3)

9. The compound according to claim 2, wherein R is maleimido-unsubstituted ethylene-unsubstituted imino-O-carbonyl-unsubstituted ethylene, n$^3$ is 1, n$^4$ is 2, X$^2$ is

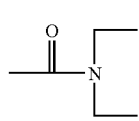

and $X^3$ is a single bond, providing formula (4):
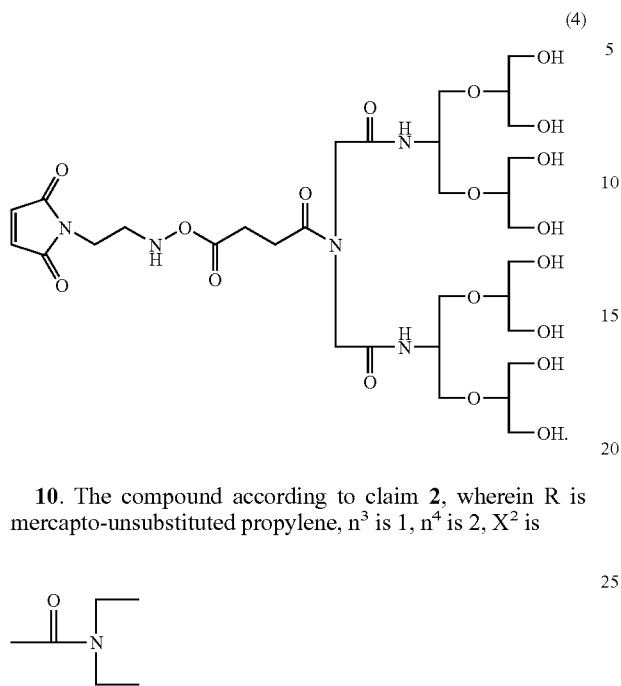
and $X^3$ is a single bond, providing formula (5):
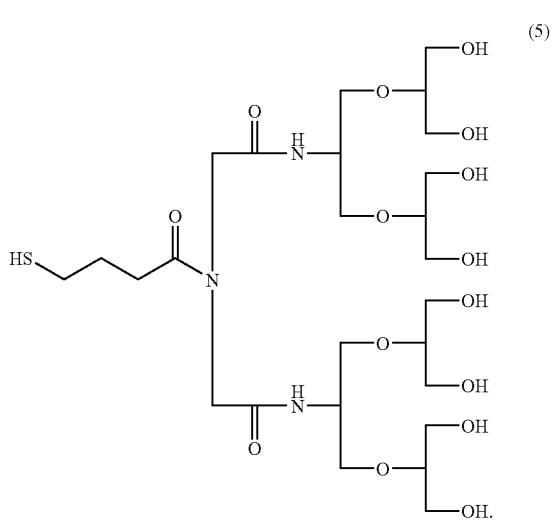
10. The compound according to claim 2, wherein R is mercapto-unsubstituted propylene, $n^3$ is 1, $n^4$ is 2, $X^2$ is
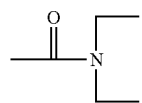
* * * * *

UNITED STATES PATENT AND TRADEMARK OFFICE
CERTIFICATE OF CORRECTION

| | |
|---|---|
| PATENT NO. | : 7,569,706 B2 |
| APPLICATION NO. | : 10/529216 |
| DATED | : August 4, 2009 |
| INVENTOR(S) | : Hisao Nemoto et al. |

It is certified that error appears in the above-identified patent and that said Letters Patent is hereby corrected as shown below:

ON THE TITLE PAGE [75]:

Inventors, "Hisao Nemoto, Tokushima (JP); Motoo Yamasaki, Tokyo (JP); Toshiyuki Suzawa, Tokyo (JP); Hiroyuki Yamaguchi, Tokyo (JP)" should read --Hisao Nemoto, Tokushima (JP); Motoo Yamasaki, Machida (JP); Toshiyuki Suzawa, Tokyo (JP); Hiroyuki Yamaguchi, Tokyo (JP)--.

ON THE TITLE PAGE [57] ABSTRACT:

Line 8, "different" should read --different.--.

COLUMN 2:

Line 33, "compound" should read --compounds--.

COLUMN 3:

Line 46, "represent" should read --represents--.

COLUMN 8:

Line 30, "a" (2nd occurrence) should read --an--;
Line 33, "a" (2nd occurrence) should read --an--; and
Line 45, "4thiazolydonyl," should read --4-thiazolydonyl,--.

COLUMN 10:

Line 4, "includes," should read --include,--;
Line 18, "antbranyl" should read --anthranyl--; and
Line 21, "a" (1st occurrence) should read --an--.

COLUMN 11:

Line 16, "B" should read --R--.

COLUMN 13:

Line 61, "Can. J. Chem., 6, 241" should read --Can. J. Chem., 62, 241--.

UNITED STATES PATENT AND TRADEMARK OFFICE
CERTIFICATE OF CORRECTION

PATENT NO. : 7,569,706 B2
APPLICATION NO. : 10/529216
DATED : August 4, 2009
INVENTOR(S) : Hisao Nemoto et al.

It is certified that error appears in the above-identified patent and that said Letters Patent is hereby corrected as shown below:

COLUMN 14:

Line 24, "has" should read --have--; and
Line 33, "being transformed" should read --transforming--.

COLUMN 16:

Line 35, "there from." should read --therefrom--; and
Line 67, "is" should read --are--.

COLUMN 17:

Line 59, "like.; and the" should be deleted.

COLUMN 18:

Line 27, "thereof" should read --thereof.--.

COLUMN 20:

Line 20, "of" (1st occurrence) should be deleted.

COLUMN 22:

Line 8, "hris(pyrrolidino)phosphonium" should read
    --tris(pyrrolidino)phosphonium--; and
Line 11, "TBF" should read --THF--.

COLUMN 28:

Line 13, "(ethyl acetate: acetic acid 100:0.7)" should read
    --(ethyl acetate: acetic acid = 100:0.7)--.

COLUMN 29:

Line 9, "CONH," should read --CONH),--.

COLUMN 30:

Line 18, "THE" should read --THF--.

UNITED STATES PATENT AND TRADEMARK OFFICE
CERTIFICATE OF CORRECTION

PATENT NO. : 7,569,706 B2
APPLICATION NO. : 10/529216
DATED : August 4, 2009
INVENTOR(S) : Hisao Nemoto et al.

It is certified that error appears in the above-identified patent and that said Letters Patent is hereby corrected as shown below:

COLUMN 37:

Line 57, "filtered" should read --filtered.--.

COLUMN 38:

Line 2, "(CHxx2)," should read --(CHx2),--.

COLUMN 39:

Line 36, "Pd(OH)OC" should read --PD(OH)$_2$/C--; and
Line 57, "(CD3OD," should read --(CD$_3$OD,--.

COLUMN 40:

Line 6, "(CD3OD," should read --(CD$_3$OD,--.

COLUMN 41:

Line 61, "J=1.0," should read --J=11.0,--.

COLUMN 50:

Line 25, "J=6.8 Hz)" should read --J=6.8 Hz).--.

COLUMN 52:

Line 56, "13C-NMR" should read --$^{13}$C-NMR--; and
Line 65, "(CH)," should read --(CH$_3$),--.

COLUMN 56:

Line 3, "(CH2)," should read --(CH$_2$),--.

COLUMN 57:

Line 6, "lizer" should read --lizers--.

UNITED STATES PATENT AND TRADEMARK OFFICE
CERTIFICATE OF CORRECTION

PATENT NO. : 7,569,706 B2
APPLICATION NO. : 10/529216
DATED : August 4, 2009
INVENTOR(S) : Hisao Nemoto et al.

It is certified that error appears in the above-identified patent and that said Letters Patent is hereby corrected as shown below:

COLUMN 59:

Lines 29-32, " 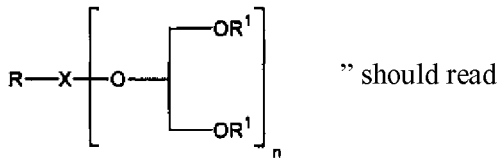 " should read

-- 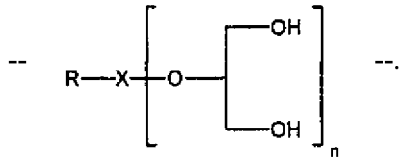 --.

COLUMN 61:

Lines 4-7, " 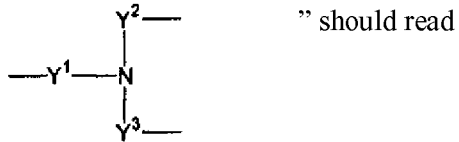 " should read

-- 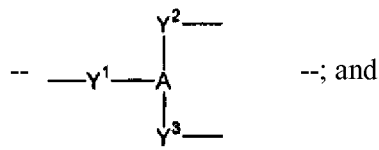 --; and

Line 11, "represent" should read --represents--.

Signed and Sealed this

Seventeenth Day of November, 2009

David J. Kappos
*Director of the United States Patent and Trademark Office*